(12) United States Patent
Oginski et al.

(10) Patent No.: US 10,004,384 B2
(45) Date of Patent: Jun. 26, 2018

(54) ROTATIONAL DEVICE AND METHOD FOR ROTATING AN ENDOSCOPE

(71) Applicant: Karl Storz SE & Co. KG, Tuttlingen (DE)

(72) Inventors: Stefan Oginski, Berlin (DE); Martin Kelp, Berlin (DE); Felix Erber, Berlin (DE)

(73) Assignee: Karl Storz SE & Co. KG, Tuttlingen (DE)

(*) Notice: Subject to any disclaimer, the term of this patent is extended or adjusted under 35 U.S.C. 154(b) by 0 days. days.

(21) Appl. No.: 14/518,785

(22) Filed: Oct. 20, 2014

(65) Prior Publication Data
US 2015/0112141 A1 Apr. 23, 2015

Related U.S. Application Data

(63) Continuation of application No. PCT/DE2013/200011, filed on Apr. 18, 2013.

(30) Foreign Application Priority Data

Apr. 18, 2012 (DE) .................. 10 2012 206 413

(51) Int. Cl.
*A61B 1/00* (2006.01)
*A61B 1/06* (2006.01)
*A61B 34/30* (2016.01)

(52) U.S. Cl.
CPC ........ *A61B 1/00121* (2013.01); *A61B 1/0016* (2013.01); *A61B 1/00105* (2013.01);
(Continued)

(58) Field of Classification Search
CPC ............ A61B 1/00174; A61B 1/00177; A61B 1/00179; A61B 1/00181; A61B 1/00045;
(Continued)

(56) References Cited

U.S. PATENT DOCUMENTS 5,325,845 A * 7/1994 Adair .................. A61B 1/0055
600/114
5,817,014 A 10/1998 Hori et al.
(Continued)

FOREIGN PATENT DOCUMENTS

DE 19609034 A1 9/1996
DE 10081782 B4 9/2005
(Continued)

OTHER PUBLICATIONS

International Search Report and Written Opinion of the International Searching Authority Application No. PCT/DE2013/200011 Completed: Aug. 14, 2013; dated Aug. 22, 2013 9 pages.

*Primary Examiner* — Ryan Henderson
(74) *Attorney, Agent, or Firm* — Whitmyer IP Group LLC

(57) ABSTRACT

A rotational device for rotating an endoscope having an operating element for moving a movable assembly of the endoscope includes a rotatable assembly, to which an endoscope is connectable, a stationary assembly, relative to which the rotatable assembly is rotatable, a first drive means for rotating the rotatable assembly relative to the stationary assembly in order to put a shaft of an endoscope connected to the rotatable assembly into rotational motion about a longitudinal axis of the endoscope, and a second drive means for moving an operating element of the endoscope connected to the rotatable assembly relative to the shaft of the endoscope in order to move an assembly of the endoscope, which assembly is movable by means of the operating element.

22 Claims, 13 Drawing Sheets

(52) U.S. Cl.
CPC ...... *A61B 1/00112* (2013.01); *A61B 1/00124* (2013.01); *A61B 1/00128* (2013.01); *A61B 1/00131* (2013.01); *A61B 1/00133* (2013.01); *A61B 1/00147* (2013.01); *A61B 1/00183* (2013.01); *A61B 1/00188* (2013.01); *A61B 1/00195* (2013.01); *A61B 1/0669* (2013.01); *A61B 1/00066* (2013.01); *A61B 2034/301* (2016.02)

(58) Field of Classification Search
CPC ............ A61B 1/00052; A61B 1/00066; A61B 1/00112; A61B 1/00114; A61B 1/00117; A61B 1/00121; A61B 1/00124; A61B 1/00126; A61B 1/00131; A61B 1/00133; A61B 1/0016; A61B 1/00195; A61B 1/04; A61B 1/042; A61B 90/361; G02B 23/2453; G03B 17/48
USPC ............... 600/109–112, 122, 136, 160–180; 348/74–76
See application file for complete search history.

(56) References Cited

U.S. PATENT DOCUMENTS

| 5,960,145 | A | * | 9/1999 | Sanchez | G02B 23/2469 |
| | | | | | 385/115 |
| 6,549,333 | B1 | | 4/2003 | Nakatate et al. | |
| 2002/0062063 | A1 | * | 5/2002 | Ogura | A61B 1/0051 |
| | | | | | 600/148 |
| 2002/0099263 | A1 | | 7/2002 | Hale et al. | |
| 2004/0140425 | A1 | | 7/2004 | Iizuka et al. | |
| 2006/0206006 | A1 | * | 9/2006 | Schara | A61B 1/00177 |
| | | | | | 600/173 |
| 2007/0030344 | A1 | | 2/2007 | Miyamoto et al. | |
| 2010/0185212 | A1 | * | 7/2010 | Sholev | A61B 34/70 |
| | | | | | 606/130 |
| 2010/0268087 | A1 | | 10/2010 | Hirota | |
| 2012/0065470 | A1 | | 3/2012 | Olds et al. | |

FOREIGN PATENT DOCUMENTS

DE          69738291 T2    9/2008
JP           2003159214 A    6/2003

\* cited by examiner

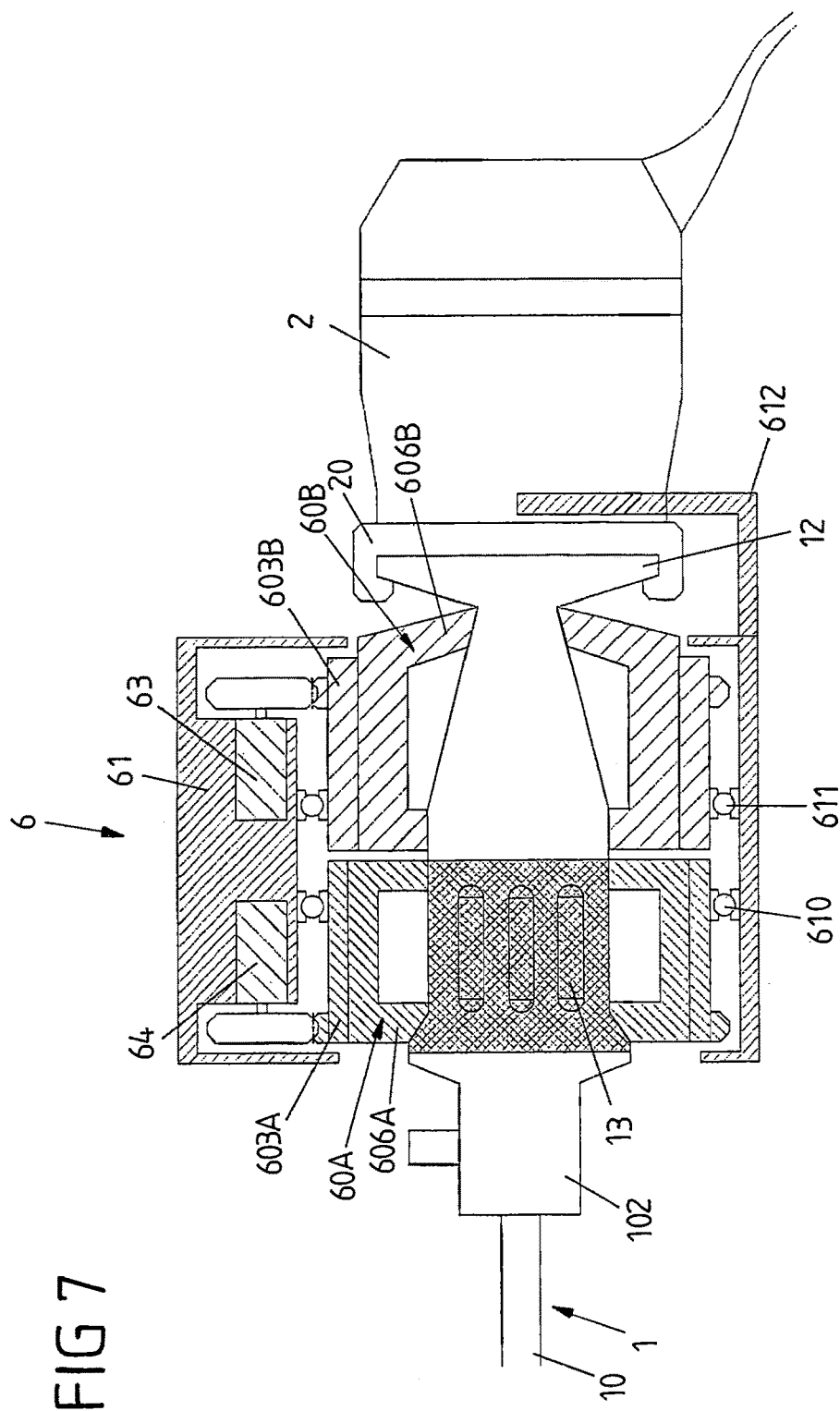

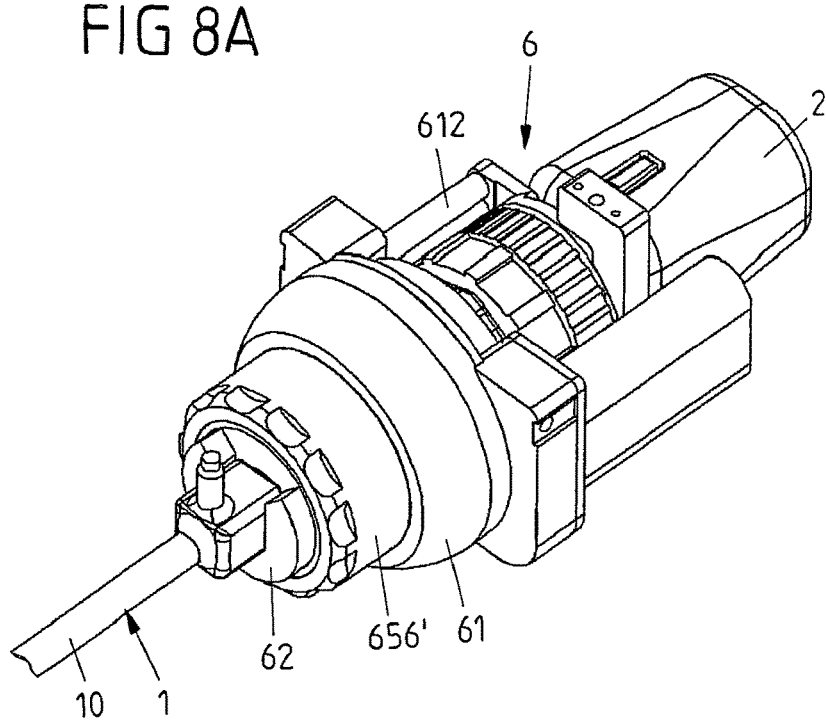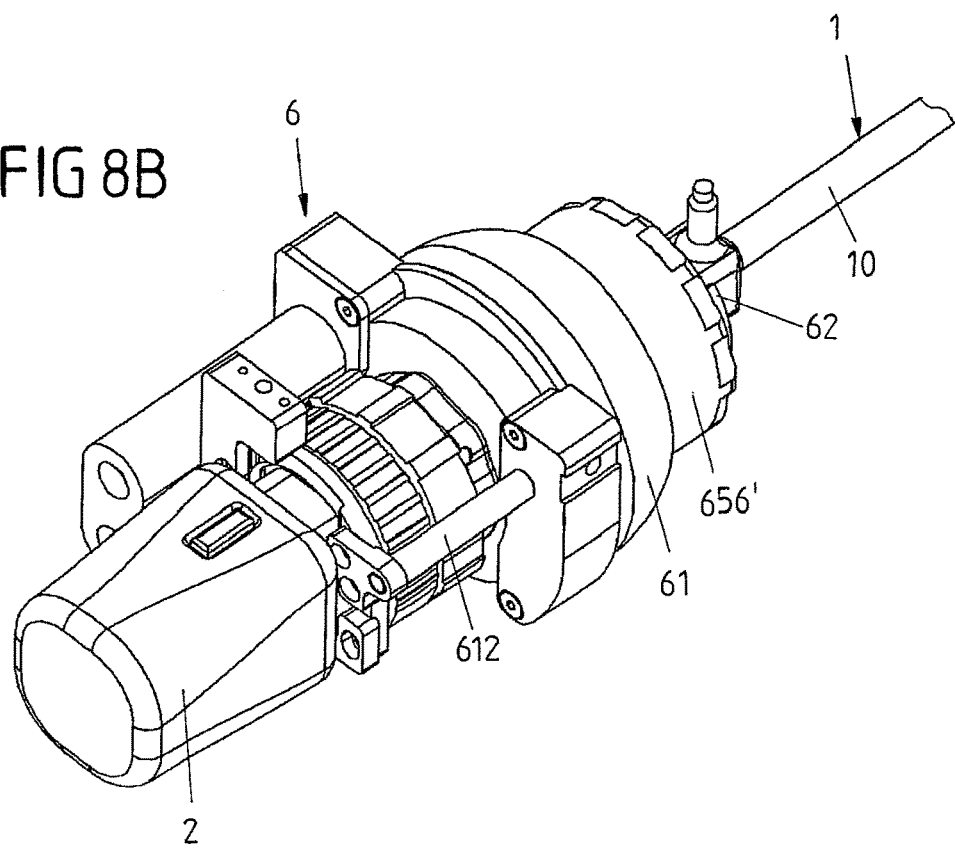

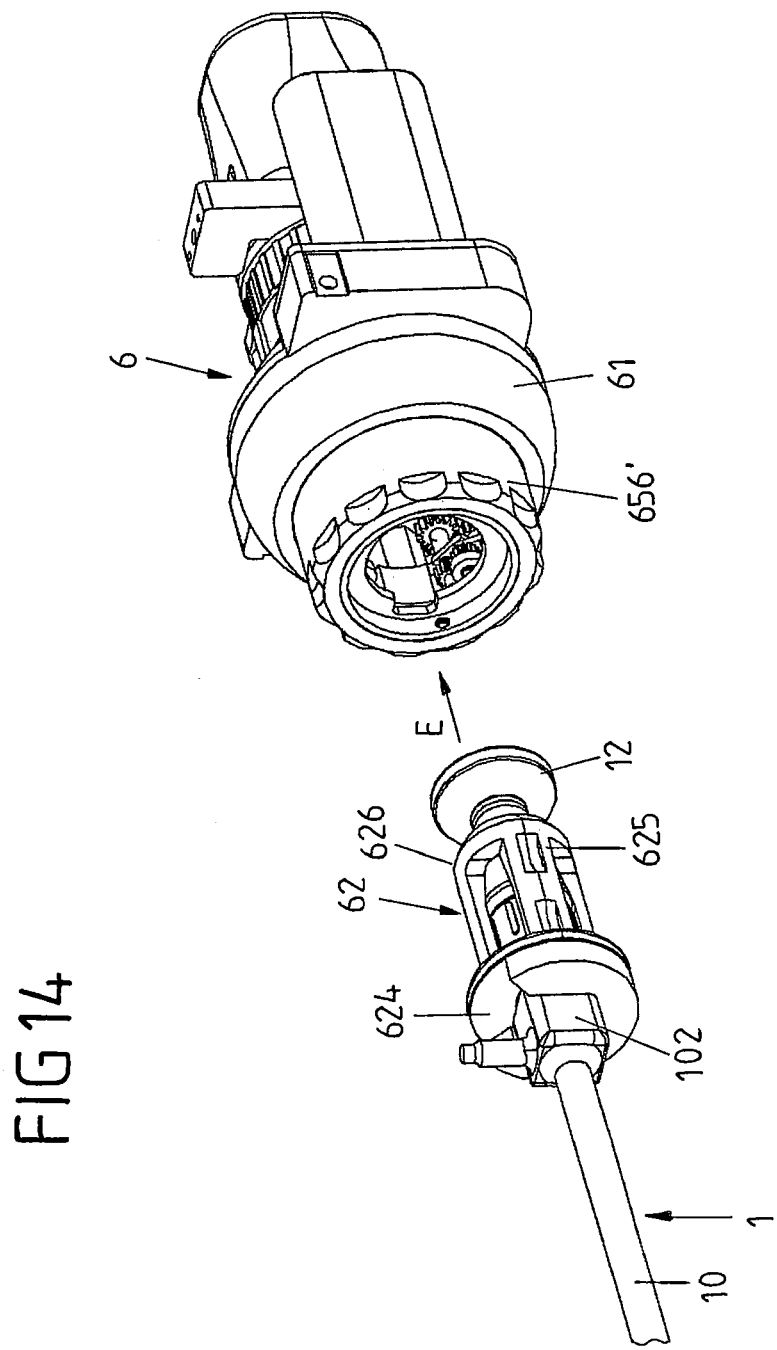

ROTATIONAL DEVICE AND METHOD FOR ROTATING AN ENDOSCOPE

FIELD OF THE INVENTION

The invention relates to a rotational device for rotating an endoscope and a method for rotating an endoscope by means of a rotational device.

Such a rotational device comprises a rotatable assembly and a stationary assembly. An endoscope can be connected to the rotatable assembly. The rotatable assembly is rotatable relative to the stationary assembly. A first drive means is embodied to put the rotatable assembly into rotational motion about a longitudinal axis so as to rotate a shaft of an endoscope connected to the rotatable assembly.

BACKGROUND OF THE INVENTION

A rotational device of the type described here can be used, in particular, for rotating a medical endoscope as is used, in particular, in micro-invasive operations on human or animal patients. Such an endoscope comprises a shaft, which is led to an operating site and, inter alia, serves to transmit light from the operating site to a camera device. The camera device registers the light and converts the latter into an analog or digital signal which is transmitted to a display device which images the operating site and therefore allows a surgeon to undertake a visual inspection of the operating site.

In the case of procedures performed micro-invasively, for example on the abdomen of the patient, a surgeon generally needs both hands to guide and operate instruments and, in this manner, perform the procedure. To date, an endoscope for optical registration and inspection of the operating site is usually held by a camera assistant, who stands e.g. behind or next to the surgeon. This may be disadvantageous because the movement space of the surgeon is restricted. Moreover, the camera assistant often needs to assume an ergonomically inexpedient body posture for a relatively long period of time, and so, with increasing operation duration, there may be blurring of the image as a result of the operation assistant tiring.

In order to make a camera assistant superfluous, holding systems, by means of which it is possible to statically assemble an endoscope on an operating table, are also used these days. Such holding systems use holding arms which have a relatively simple design and are universally usable, but only facilitate a manual change in the position of the endoscope by way of adjusting the holding arm.

In place of such holding systems, mechanical, in particular mechatronic guide systems, which facilitate a motor-driven adjustment of the position of an endoscope, are also known. By way of example, a guide system known from DE 196 09 034 A1 facilitates both the pivoting of an endoscope about a pivot point, which, in particular, corresponds to a penetration point at an abdominal wall of a patient or a different access opening at a patient, and the rotating of said endoscope about the longitudinal axis thereof.

In the guide system of DE 196 09 034 A1, this is achieved by virtue of an adapter being attached to a housing of the endoscope, which adapter is coupled via a spur gear with a further spur gear of a drive device in such a way that the endoscope can be put into rotational motion, driven by the drive device. A camera device receiving the light from the endoscope is held in a stationary manner in this case by virtue of the camera device being arranged at a holder holding the drive device by means of a retainer. Thus, the endoscope is rotated relative to the camera device.

The guide system as per DE 196 09 034 A1 facilitates a rotation of the endoscope about the longitudinal axis thereof and a corresponding setting of the field of view. By way of example, in the case of an endoscope which, by means of a suitable optical unit (a so-called "side-view tip"), receives light from a region lateral to the endoscope shaft, the fixed or adjustable direction of view of which endoscope is not parallel to the longitudinal axis of the endoscope shaft, the field of view can be pivoted by rotating the endoscope about the longitudinal axis thereof and an operating site can be observed from different observation directions.

DE 101 41 226 C1 has disclosed an endoscope holder and transport unit which has a drive sleeve to be brought into contact with a shaft of an endoscope. The drive sleeve can be driven and rotated about the longitudinal axis in order to rotate the endoscope about the longitudinal axis thereof.

U.S. Pat. No. 5,540,649 has disclosed a positioning means for medical instruments which comprises a drive wheel, driven by a drive device, for positioning an endoscope, in particular along the longitudinal axis thereof.

The field of view, in which light from the region of an operating site can be recorded by means of a camera device, can be expanded and varied by a rotational device for rotating an endoscope by virtue of the endoscope being rotated and, as a result thereof, the field of view being pivoted about the longitudinal axis of the endoscope.

Moreover, endoscopes are known which comprise one or more operating elements, for example for adjusting an optical unit arranged at a distal end of the endoscope, and by means of which, for example, a field of view can be varied, a zoom setting can be adjusted or a focus setting can be modified. Conventionally, as a component of an endoscope to be operated by hand overall, such operating elements may be operated by hand.

In principle, there is a need for guide systems for endoscopes which facilitate a motor-driven rotation of such an endoscope about the longitudinal axis thereof, which endoscope is, in principle, to be operated by hand, and, at the same time, also facilitate simple handling of the endoscopes.

An object of the present invention is to provide an improved rotational device, an improved endoscope device and an improved method for rotating an endoscope which, in particular, facilitate simple handling of an endoscope comprising an operating element.

SUMMARY OF THE INVENTION

This object is achieved by the subject matter of the present teachings.

Embodiments of the present invention are based on the concept of providing a second drive means in a rotational device for rotating an endoscope which comprises a first drive means for driving a rotatable assembly for rotating a shaft of an endoscope connected to the rotatable assembly, which second drive means is embodied to adjust an operating element of the endoscope connected to the rotatable assembly relative to the shaft of the endoscope in order to actuate an assembly of the endoscope to be operated by means of the operating element.

The present invention proceeds from the idea of providing at least two drive means for a rotational device, which drive means serve, firstly, for rotating an endoscope connected to the rotational device and, secondly, for actuating an operating element provided at the endoscope. The first drive means drives a rotatable assembly, to which a shaft of an endoscope is coupleable or detachably mechanically connectable such that, by way of rotating the rotatable assembly, the endoscope can be rotated about the longitudinal axis along which the shaft extends. The second drive means serves for adjusting or moving the operating element provided on the endoscope, wherein, by way of the second drive means, the operating element can be adjusted relative to the shaft and therefore independently of a rotational motion of the shaft.

The first drive means can be arranged at the stationary assembly and/or at the rotatable assembly and generates a torque for rotating the rotatable assembly relative to the stationary assembly. The first drive means comprises, in particular, an electric motor, an ultrasonic motor, a piezomotor or any other motor.

Provision can be made for a single second drive means for actuating an operating element. Alternatively, provision can be made for a plurality of second drive means which are embodied for actuating a plurality of different operating elements. The second drive means or each one of the second drive means comprises, in particular, an electric motor, an ultrasonic motor, a piezo-motor or any other motor.

The operating element can be embodied as rotatable operating wheel which, in particular, is rotatable about the longitudinal axis of the endoscope. Alternatively, the operating element can be embodied as a slider, lever or the like.

The second drive means is preferably embodied, by way of actuating the operating element, to bring about a change in a direction of view of the endoscope by moving an optical element, in particular an optical element arranged within the endoscope and movable relative to the endoscope, for example a swivel prism, a mirror or a lens, or a change in a focus or zoom setting.

The rotational device is preferably embodied as a modular unit and can be used together with an endoscope which is designed for manual operation per se. The endoscope can be rotated by means of the first drive means which engages on a conventional shaft of the endoscope. An operating element, which is provided for a manual adjustment, can be rotated or moved along a straight or curved path by means of the second drive means, wherein the second drive means acts on the operating element by means of suitable means for adjustment.

The second drive means can be arranged at the rotatable assembly. In this case, the second drive means is also moved in the case of a rotation of the endoscope by means of the first drive means. Then, independently of the rotation of the endoscope by means of the first drive means, the operating element can be adjusted by means of the second drive means in order to adjust an assembly to be operated by means of the operating element, for example an optical unit of the endoscope.

Alternatively, the second drive means can be arranged at the stationary assembly. This is explained in more detail below.

The second drive means is preferably embodied to rotate the operating element of the endoscope about the longitudinal axis. By way of example, the operating element can be arranged as a ring-shaped element at the endoscope and be rotatable relative to the shaft about the longitudinal axis of the shaft. In order to adjust the assembly to be operated by means of the operating element, the operating element can be rotated about the longitudinal axis, along which the shaft extends, by means of the second drive means.

The rotatable assembly which is driven by the first drive means is, in particular, coupled to the endoscope in a rotationally secured manner by means of an adapter or a clamping means. Therefore, the rotatable assembly is connected to the endoscope in a rotationally secured manner in a force-fit or frictionally engaged and/or interlocking manner by means of the adapter or the clamping means. That is why the endoscope can be rotated about the longitudinal axis thereof by driving the rotatable assembly by means of the first drive means and by the resulting rotation of the rotatable assembly relative to the stationary assembly.

If the operative connection of the rotatable assembly to the endoscope is established by means of an adapter, the adapter is preferably removable from the rotatable assembly along the longitudinal axis in order to separate the endoscope from the rotatable assembly or joinable to the rotatable assembly along the longitudinal axis in order to bring the endoscope into a rotationally secured operative connection with the rotatable assembly. To this end, the adapter can be embodied in the form of a substantially rotationally symmetric basket which, for joining and attaching the endoscope to the rotatable assembly, joins to the rotatable assembly along the longitudinal axis, for example by being inserted or introduced into a suitable receptacle opening on the rotatable assembly. In the inserted state, the adapter is secured on the rotatable assembly in a rotationally secured manner. The mechanical connection between adapter and rotatable assembly can be released in order, once again, to bring the adapter out of engagement from the rotatable assembly along the longitudinal axis and therefore to detach the endoscope from the rotatable assembly.

The adapter is, in particular, assembled from two adapter parts movable relative to one another, which are embodied to hold the endoscope between them in a rotationally secured manner. By way of example, the adapter parts are hinged to one another by means of a hinge such that the adapter parts can be pivoted relative to one another in order to be able to open the adapter and insert the endoscope into the adapter. In the closed state, the adapter parts surround a section of the endoscope near the proximal end of the endoscope completely or substantially completely in the circumferential direction. One or more interlocking sections can be provided on one or both adapter parts, which, in the closed state of the adapter, abut against an associated interlocking section on the shaft of the endoscope or on another part of the endoscope around the longitudinal axis in an interlocking manner in the circumferential direction in order in this way to hold the endoscope in a force-fit or frictionally engaged and/or interlocking rotationally secured manner.

By virtue of the adapter, in a state in which it is coupled to the rotatable assembly, being connected to the rotatable assembly in a force-fit or frictionally engaged and/or interlocking rotationally secured manner and also in an axially secured manner along the longitudinal axis, rotation of the rotatable assembly can transmit an adjustment force without slip to the adapter and, by means thereof, to the endoscope for rotating the endoscope about the longitudinal axis thereof.

For rotating the endoscope, the rotatable assembly is driven about the longitudinal axis thereof by means of the first drive means. To this end, the first drive means can have an operative connection to the rotatable assembly via a gearing, for example via a friction wheel, a pinion, a worm drive or a chain drive, wherein the friction wheel or the pinion is arranged at a driveshaft of the drive means and an adjustment force can be introduced into the rotatable assembly and, by means thereof, into the endoscope by rotating the friction wheel or the pinion.

Alternatively, other configurations, for example an embodiment without gearing, are possible, wherein the first drive means is embodied, in particular, as hollow rotor motor, ultrasonic motor or piezo-motor without gearing.

The second drive means, which serves for adjusting the operating element, can be embodied to introduce an adjustment force into the operating element via a gearing, e.g. a friction wheel, a pinion, a worm drive or a chain drive. If a friction wheel is provided, the latter can, for example, abut directly against the operating element such that the friction wheel, driven by the second drive means, transmits a rotational motion to the operating element and, by means thereof, adjusts the operating element. If the second drive means drives a pinion, the latter can, for example, act on a second rotatable assembly which has an operative rotationally secured connection to the operating element by means of a clamping means or an adapter such that the second rotatable assembly can be rotated, driven by the pinion, and, by means thereof, the operating element can be adjusted.

The second drive means can also be embodied without gearing and, for example, comprise a hollow rotor motor, an ultrasonic motor or a piezo-motor.

If a friction wheel is provided for transmitting force to the operating element, the friction wheel is, in particular, arranged at a lever arm of a pivotable lever, wherein, in an abutting position of the lever, the friction wheel abuts against the operating element of the endoscope connected to the rotatable assembly. The friction wheel is elastically pretensioned in the direction toward the abutting position in particular. By way of example, the lever is elastically pretensioned in the direction of the abutting position of the friction wheel by virtue of a mechanical spring engaging on the lever and pressing the lever with the friction wheel arranged thereon in the direction of the abutting position of the friction wheel. Therefore, in the abutting position, the friction wheel is in a frictional operative connection with the operating element or coupled to the latter in a force-fit or frictionally engaged manner such that the operating element is driven by a rotational motion of the friction wheel. The lever can be pivoted and, by means thereof, the friction wheel can be removed from an abutting position by a suitable actuating element in order to lift the operative connection between the friction wheel and the operating element such that the endoscope can be removed from the rotational device without damaging the friction wheel mechanism.

The actuating element can be embodied as a handwheel rotatable about the longitudinal axis, which handwheel is rotatably arranged at the rotatable assembly. Rotating the handwheel through a predetermined angle can cause a movement of the friction wheel from the abutting position. Alternatively, the actuating element can be configured as an actuation lever which can be actuated for pivoting the lever carrying the friction wheel.

If the actuating element is configured as a handwheel, it is, for example, arranged at the rotatable assembly in a manner pivotable relative to the rotatable assembly or rotatable about the longitudinal axis and elastically pretensioned in relation to the rotatable assembly, for example by means of mechanical spring.

In particular, in the case of a rotational device, as is described here, the first drive means drives a first rotatable assembly which is connectable to the endoscope, and the second drive means arranged at the stationary assembly drives a second rotatable assembly which is coupleable to, or to be brought into an operative connection with, the operating element of the endoscope. In this case, the second drive means, just like the first drive means, is arranged at the stationary assembly. The first drive means drives the first rotatable assembly in order to rotate the endoscope. The second drive means drives the second rotatable assembly in order, by means thereof, to rotate the operating element or to adjust in a different manner.

In particular, the first drive means and the second drive means for, firstly, rotating the endoscope and, secondly, moving or adjusting the operating element are partly or completely independent of one another. If the endoscope is intended to be rotated by means of the first drive means, the second drive means for adjusting the operating element about the longitudinal axis is to be operated with the same speed as the first drive means so that the operating element is not rotated relative to the shaft of the endoscope. If there is a relative velocity between the endoscope and the operating element when rotating the endoscope by means of the first drive means, this relative velocity causes an adjustment of the operating element. If the operating element is not to be adjusted relative to the shaft, the second drive means is to be operated during a rotation of the endoscope in such a way that no relative motion occurs between the operating element and the shaft of the endoscope.

If the operating element is to be adjusted, the second drive means is supplied with power, in particular with current, when the shaft of the endoscope is not rotated. If the operating element is to be adjusted simultaneously also with a rotation of the endoscope, a suitable relative motion can be caused by a speed difference in the rotational speeds of the shaft of the endoscope and of the operating element.

The drive means respectively comprise e.g. a servo motor or a regulated DC motor or a synchronous or asynchronous AC motor or a stepper motor, and are, in particular, electronically controlled.

The first and the second rotatable assembly can respectively comprise a ring element rotatable about the longitudinal axis relative to the stationary assembly, which ring element is engaged via a toothing to a pinion of the respectively assigned drive means and serves for transmitting an adjustment force and a torque, in the case of, respectively, a transmission to the shaft in the first case and to the operating element of the endoscope in the other case. The ring elements can in each case be connected in a rotationally secured manner to the shaft of the endoscope and the operating element, respectively, by means of a clamping means or a suitable adapter. Alternatively, the ring element can in turn drive a friction wheel mechanism, by means of which an adjustment force is transmitted to the shaft or to the operating element.

In the case of a rotational device, as is described here, provision is made, in particular, for a light source for feeding or coupling light into the endoscope. The light source can be arranged at the rotatable assembly and, during the operation, be rotated with the rotatable assembly. Here, by means of one or more contacts, the light source is connected in an electrically conducting manner to an appropriate number of slip rings at the stationary assembly such that the light source can be supplied with electric power by means of an electrical connector at the stationary assembly. If provision is made for only one contact and one slip ring, a circuit for supplying the light source is closed, in particular, by means of other electrically conductive components of the rotational device.

An endoscope device comprises a rotational device of the type described above and an endoscope arranged at the rotatable assembly. In particular, the endoscope comprises a shaft and an operating element for changing a direction of view of the endoscope by moving an optical element, in particular an optical element arranged within the endoscope and movable relative to the endoscope, for example a swivel prism, a rotational lens or a rotational mirror, or for changing a focus or zoom setting of an optical system of the endoscope. By way of example, provision is made for a swivel prism swivelable about a swivel axis and arranged at distal end distant from the rotational device, and which can be adjusted by means of the operating element. The rotational device acts on the operating element via the second drive means and is therefore designed to adjust the swivel prism.

A swivel prism facilitates swiveling of a field of view about the swivel axis assigned to the swivel prism. Here, swiveling of the field of view is only possible in one plane, namely in the plane transverse to the swivel axis. By an additional rotation of the endoscope, driven by the first drive means, the plane in which the swivel prism can be swiveled can be rotated such that the light from a large space can be registered by the superposed rotation of the endoscope and the swivel movement of the swivel prism, and guided to a camera device connected to the endoscope by means of the endoscope. By way of example, in the case of a medical endoscope this facilitates the inspection of an operating site in a large region, without, to this end, the position of the endoscope in space per se needing to be adjusted (except for the rotational position of the endoscope).

The object is also achieved by a method for rotating an endoscope by means of a rotational device, in which an endoscope is connected to a rotatable assembly of the rotational device and a first drive means puts the rotatable assembly into rotational motion about a longitudinal axis relative to a stationary assembly of the rotational device for the purposes of rotating a shaft of the endoscope connected to the rotatable assembly. Here, provision is made for a second drive means of the rotational device to adjust, relative to the shaft of the endoscope, an operating element of the endoscope connected to the rotatable assembly for the purposes of actuating an assembly of the endoscope to be operated by the operating element.

In a method for handling an endoscope, the endoscope is coupled to a rotatable assembly of a rotational device, the rotatable assembly is rotated relative to a stationary assembly of the rotational device by means of a first drive means in order to put a shaft of the endoscope connected to the rotatable assembly into rotational motion about a longitudinal axis of the endoscope, and an operating element of the endoscope coupled to the rotatable assembly is moved by means of a second drive means of the rotational device in order to move an assembly, to be moved by means of the operating element, of the endoscope relative to the shaft of the endoscope.

The advantages and advantageous embodiments described above for the rotational device analogously also find application to the method.

BRIEF DESCRIPTION OF THE DRAWINGS

The concept on which the invention is based should be explained in more detail in the following on the basis of the exemplary embodiments depicted in the figures. In detail:

FIG. 7 shows a schematic sectional illustration of a further rotational device for rotating an endoscope;

FIG. 8A shows a schematic axonometric illustration of a further rotational device for rotating an endoscope;

FIG. 8B shows a further schematic axonometric illustration of the rotational device from FIG. 8A;

FIG. 14 shows a further schematic axonometric illustration of the rotational device from FIGS. 8A to 13B where the adapter is separated from the rotatable assembly.

DETAILED DESCRIPTION OF THE INVENTION

Figure 1:
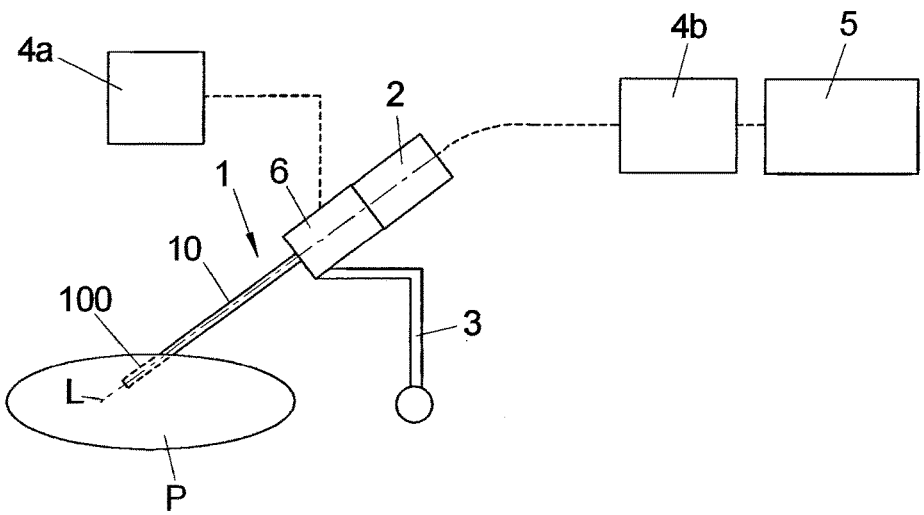
FIG. 1 shows a schematic illustration of an endoscope device.

FIG. 1 shows a schematic illustration of an endoscope device comprising an endoscope 1 and, connected thereto, a camera device 2 serving for recording or registering images from an operating site at a patient P. The endoscope 1 comprises a shaft 10 with a longitudinal axis L, the distal end 100 of which is guided to the patient P and inserted into the patient P. Light from the operating site can be guided to the camera device 2 by the shaft 10 of the endoscope 1, said camera device converting the light into analog or digital and, in particular, electrical signals and feeding these to an evaluation unit 4b. The evaluation unit 4b processes the signals. The signals are transmitted to a display device 5 in the form of a monitor for displaying images of the operating site.

A holder 3 is fastened to e.g. an operating table. The holder 3 holds a rotational device 6 which holds the endoscope 1. The rotational device 6 facilitates a rotation of the endoscope 1 about the longitudinal axis L of the shaft 10 and, in this manner, a variation, in particular a swiveling, of a field of view of the endoscope 1.

The control unit 4a serves for controlling the rotational device 6. The control unit 4a and the evaluation unit 4b can be embodied as separate units or, deviating from the illustration FIG. 1, can be coupled for interchanging signals or can be combined mechanically and/or functionally to form a unit.

Figure 2:
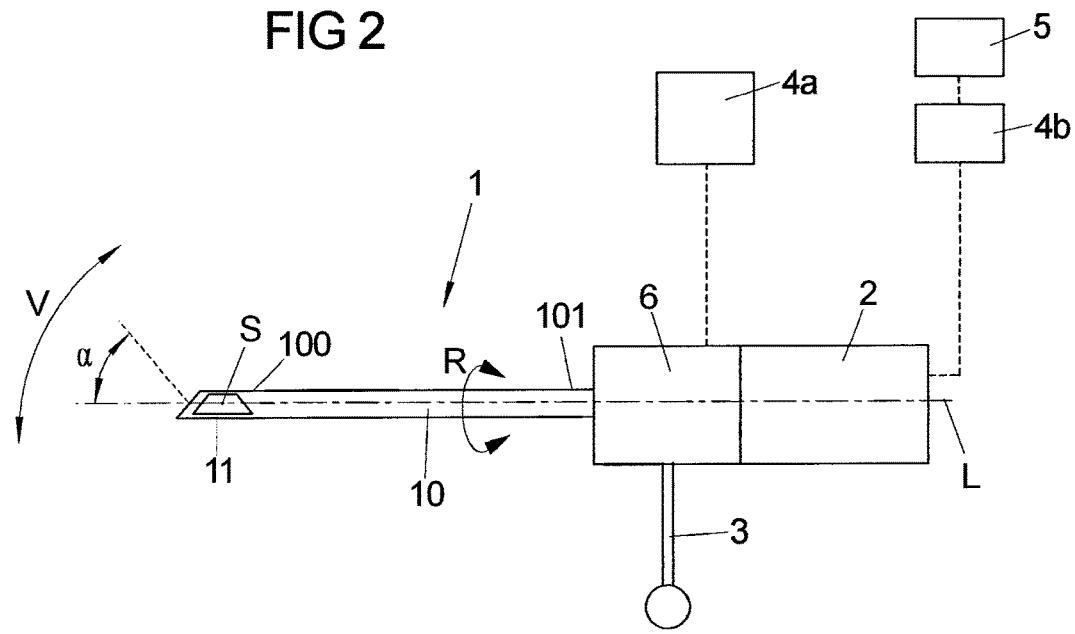
FIG. 2 shows a schematic illustration of a further endoscope device.

FIG. 2 shows a schematic illustration of a further endoscope device which, in terms of some features and properties, is similar to the endoscope device depicted above on the basis of FIG. 1. The following illustrates in particular features and properties in which the endoscope device from FIG. 2 differs from the endoscope device from FIG. 1.

In the endoscope device depicted in FIG. 2, the endoscope 1 comprises a swivel prism 11 (may also be referred to as a pivotable prism) at its distal end 100. The swivel prism 11 is swivelable about a swivel axis S, for example by means of a motor integrated into the endoscope, by means of a push or pressure rod, or in any other way. The swivel axis S is orthogonal to the longitudinal axis L of the shaft 10 and orthogonal to the plane of the drawing in FIG. 2. The swivel prism 11 can be used to register light from an in particular conical field of view which is describable by a viewing angle α. By swiveling the swivel prism 11 about the swivel axis S (swivel movement V), it is possible to vary the field of view, in particular to swivel it in a plane perpendicular to the swivel axis S. By rotating the shaft 10 of the endoscope 1 by means of the rotational device 6, it is additionally also possible to rotate the field of view about the longitudinal axis L (rotational movement R) such that an operating site can be observed in a large spatial region by, firstly, swiveling the swivel prism 11 and, secondly, rotating the shaft 10 of the endoscope 1.

As an alternative to the depicted swivel prism, the endoscope may comprise different means for setting or modifying the direction of view, for example an arrangement with one or more rotatable or swivelable lenses and/or mirrors. In particular, the endoscope 1 may comprise an arrangement of two reflecting surfaces, as is known from periscopes. Alternatively, the distal end of the endoscope can be mechanically angleable.

The proximal end 101 of the endoscope 1 is mechanically connected to the rotational device 6 and the camera device 2. The endoscope device is held in its position by the holder 3 engaging at the rotational device 6.

For interchanging electrical or other signals and for transmitting power, the camera device 2 is coupled to the evaluation unit 4b. For interchanging electrical or other signals and for transmitting power, the rotational device 6 is coupled to the control unit 4a. The evaluation unit 4b serves to receive and evaluate signals from the camera device 2 and feed said signals to the display device 5. At the same time, the control unit 4a can control the rotational device 6 and, by means thereof, both the rotation of the endoscope 1 and the swiveling of the swivel prism 11 in order to set and modify the rotational position of the shaft 10 and the position of the swivel prism 11.

Figure 3:
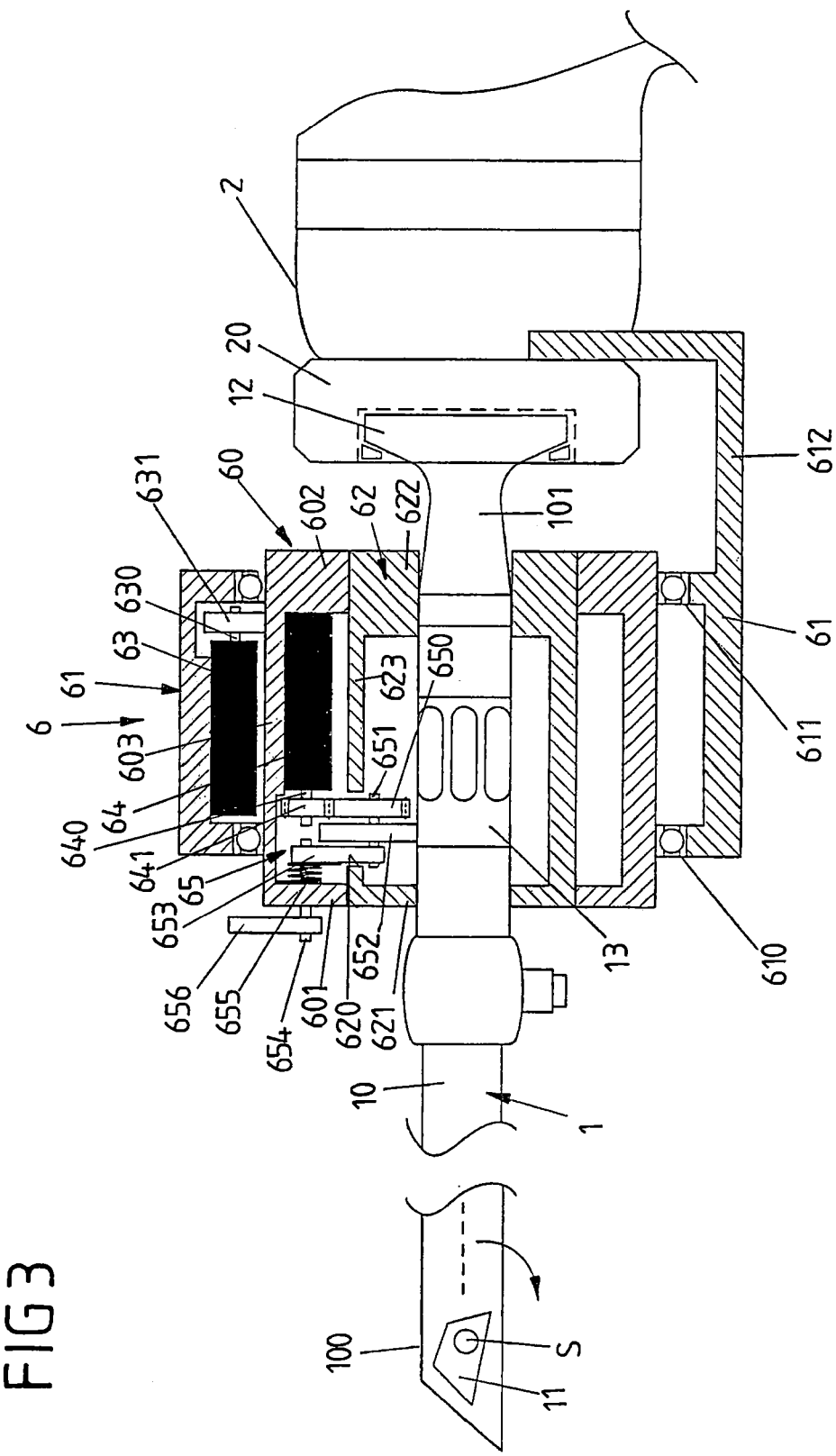
FIG. 3 shows a schematic sectional illustration of a rotational device for rotating an endoscope.

FIG. 3 shows a schematic sectional illustration of a rotational device 6 which, in terms of some features and properties, is similar to the rotational device depicted above on the basis of FIGS. 1 and 2. Furthermore, FIG. 3 indicates, using contours, an endoscope 1 and a camera device 2. The sectional plane in FIG. 3 contains the longitudinal axis L of the shaft 10 of the endoscope 1. The rotational device 6, the endoscope 1 and the camera device 2 may have features and properties which are similar to the ones depicted above on the basis of FIGS. 1 and 2. In particular, the rotational device 6 depicted in FIG. 3 is one of the rotational devices depicted above on the basis of FIGS. 1 and 2.

The rotational device 6 is embodied for rotating the endoscope 1 and the direction of view of the endoscope 1 about the longitudinal axis L of the endoscope. Furthermore, the rotational device 6 is embodied to actuate an actuation means or an operating element 13 at the proximal end 101 of the endoscope 1, in particular rotate said actuation means or operating element about the longitudinal axis L.

The operating element 13 is provided and embodied for swiveling the swivel prism 11, which is arranged at the distal end 100 of the endoscope 1 and swivelable about the swivel axis S, and thereby varying a field of view of the endoscope 1, in particular swiveling the direction of view of the endoscope 1 about the axis S. To this end, the operating element 13 can be adjusted, in particular rotated, about the longitudinal axis L of the endoscope 1, wherein the swivel prism 11 can be swiveled about the swivel axis S thereof by the adjustment movement of the operating element 13.

The rotational device 6 comprises a stationary assembly 61, which supports or holds the camera device 2 by means of a support section 612. By way of example, the rotational device 6 is fastened to an operating table by a holder 3 (see FIGS. 1 and 2). A rotatable assembly 60 is rotatably mounted about the longitudinal axis L at the stationary assembly 61 by means of bearings 610, 611. The bearings 610, 611 are respectively embodied, in particular, as a roller bearing or another antifriction bearing or as a sliding bearing. A drive means 63 comprising a driveshaft 630 is arranged at the stationary assembly 61. A friction wheel 631 at the driveshaft 630 rolls on a cylindrical barrel surface 603 of the rotatable assembly 60 in order to put the rotatable assembly 60 into rotational motion about the longitudinal axis L.

The rotatable assembly 60 has a rotationally secured operative connection to the shaft 10 of the endoscope 1 via an adapter 62. To this end, the adapter 62 is held between limbs or radially inwardly projecting collars or support sections 601, 602 of the rotatable assembly 60 in a force-fit or frictionally engaged and/or interlocking manner and it has a rotationally secured, e.g. force-fit or frictionally engaged and/or interlocking connection to the shaft 10 of the endoscope 1 via limbs or radially inwardly projecting collars or support sections 621, 622.

The rotational device 6 has a substantially or at least partly rotationally symmetric design. In particular, the stationary assembly 61 has a substantially cylindrical, in particular cylinder barrel-shaped or circular cylinder barrel-shaped design with a cylindrical ring element extending around the circumferential direction. The rotatable assembly 60 consists substantially of the cylindrical barrel surface 603 and the circumferential limbs 601, 602 formed like annular collars.

If the rotatable assembly 60, driven by the drive means 63, is put into rotational motion about the longitudinal axis L, the endoscope 1 is likewise rotated about the longitudinal axis L by virtue of the shaft 10 of the endoscope 1 being taken along by the adapter 62 in the case of rotational motion of the rotatable assembly 60.

A drive means 64 is provided on the rotatable assembly 60, said drive means serving to drive a friction wheel mechanism 65 for adjusting the operating element 13 relative to the shaft 10. The drive means 64 comprises a driveshaft 640 and is engaged to a gearwheel 650 of the friction wheel mechanism 65 via a pinion 641 on the driveshaft 640. The gearwheel 650 is arranged on a shaft 651 and, via the shaft 651, transmits rotational motion to a friction wheel 652 which has a frictionally engaged connection to the operating element 13.

The shaft 651 is arranged on a pivotable lever 653 in such a way that it can be displaced along a circular arc. The lever 653 is coupled to an actuating element in the form of an actuation lever 656 via a shaft 654. The lever 653 is pretensioned by a spring 655 in the direction of an abutting position, in which the friction wheel 652 abuts against the operating element 13. By means of the actuation lever 656, the lever 653 can be pivoted about the shaft 654 in order, in this manner, to remove the friction wheel 652 from the operating element 13 and therefore bring it out of contact with the operating element 13.

In a ready-for-use position or in a work mode, the friction wheel mechanism engages through an opening 620 at the adapter 62. By pivoting the actuation lever 656, the friction wheel mechanism 65 can be removed from the opening 620 and therefore be brought into an interchange mode. In the interchange mode, the adapter 62 with the endoscope 1 can be removed along the longitudinal axis L from the rotatable assembly 60 and thereby the endoscope 1 can be released or separated from the rotational device 6.

The endoscope 1 has a rotationally secured connection to the rotatable assembly 60 and, driven by the first drive means 63 at the stationary assembly 61, can be rotated about its longitudinal axis L. Independently thereof, the operating element 13 can be moved by the second drive means 64 by means of the friction wheel mechanism 65 in order, in this manner, to adjust the swivel prism 11.

In this manner, the field of view of the endoscope 1 can be varied over a large range by virtue of, firstly, the swivel prism 11 being adjusted in a plane orthogonal to the swivel axis S and, secondly, this plane being able to be rotated by rotating the endoscope 1 about the longitudinal axis L. In this manner, for example in the case of an embodiment of the endoscope 1 as a medical endoscope, an operating site can be inspected and monitored over a large field of view.

The rotational device 6 is embodied to operate an endoscope 1 which, per se, is provided for manual actuation. In particular, it is possible to rotate the operating element 13, which is provided for manual actuation, and, by means thereof, adjust the swivel prism 11 in a motorized manner by means of the second drive means 64. The adapter 62 can be adapted to the specific design of an endoscope from a specific manufacturer, while other parts of the rotational device 6 may be suitable at the same time for different designs of the endoscopes and, in particular, also for the endoscopes from different manufacturers. Thus, in particular, only the adapter 62 needs replacement when interchanging the endoscope.

With the proximal end 101 thereof, which can be embodied as an eyepiece 12 (may also be referred to as the cup of an eyepiece) pursuant to DIN 58105, the endoscope 1 is connected to a coupling means 20 of the camera device 2. The camera device 2 is kept stationary in terms of position in relation to the stationary assembly 61 when rotating the endoscope 1. The coupling means 20 of the camera device 2 is embodied to hold or guide the eyepiece 12 in the axial and radial direction but at the same time permit rotational motion of the eyepiece 12 relative to the camera device 2.

Figure 4:
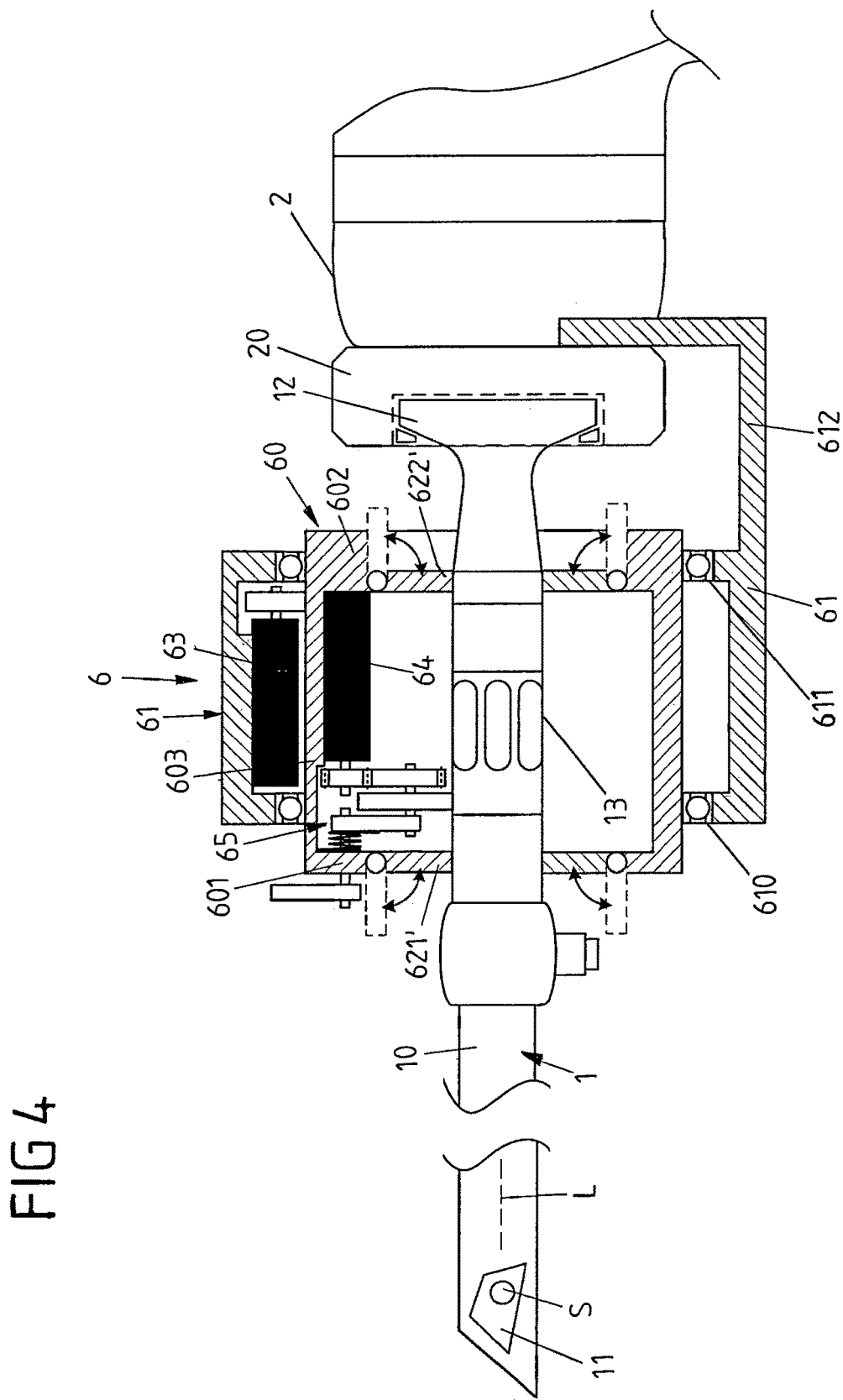
FIG. 4 shows a schematic sectional illustration of a further rotational device for rotating an endoscope.

FIG. 4 shows a schematic sectional illustration of a rotational device 6 which, in terms of some features and properties, is similar to the rotational devices depicted above on the basis of FIGS. 1 to 3. The type of illustration, in particular the sectional plane, corresponds to that in FIG. 3. In particular, an endoscope 1 and a camera device 2 are also indicated by contours in FIG. 4. The following illustrates in particular features and properties in which the rotational device 6 differs from the rotational devices depicted above on the basis of FIGS. 1 to 3.

In particular, the rotational device 6 depicted in FIG. 4 differs from the rotational devices depicted above on the basis of FIGS. 1 to 3 in that no separate, additional adapter 62 is provided for connecting the rotatable assembly 60 to the shaft 10 of the endoscope 1. Rather, a clamping means 621', 622' in the form of clamping limbs arranged in a swivelable manner on the limbs 601, 602 of the rotatable assembly 60 is provided on the rotatable assembly 60. For the purposes of a rotationally secured connection between the shaft 10 of the endoscope 1 and the rotatable assembly 60, the clamping limbs 621', 622' are brought into abutment with the shaft 10.

The clamping limbs 621', 622' are, in particular, held in the positions depicted in FIG. 4 by solid lines and shading by means of a latch (not shown in FIG. 4) and/or by one or more springs. The clamping limbs 621', 622' can be put into the positions depicted by dashed lines after releasing the latch and/or against the force of the spring or springs, in which positions they do not abut against the endoscope 1 and the endoscope can be removed from the rotational device 6.

The surfaces of the clamping limbs 621', 622' destined for abutting at the shaft 10 of an endoscope 1 are embodied in terms of their surface properties and/or surface structure in such a way that the shaft 10 of the endoscope 1 is connected in a frictionally engaged or force-fit and/or interlocking rotationally secured manner to the rotatable assembly 60 of the rotational device 6.

In terms of further features and properties, the rotational device 6 corresponds, in particular, to the rotational device depicted above on the basis of FIG. 3.

Figure 5:
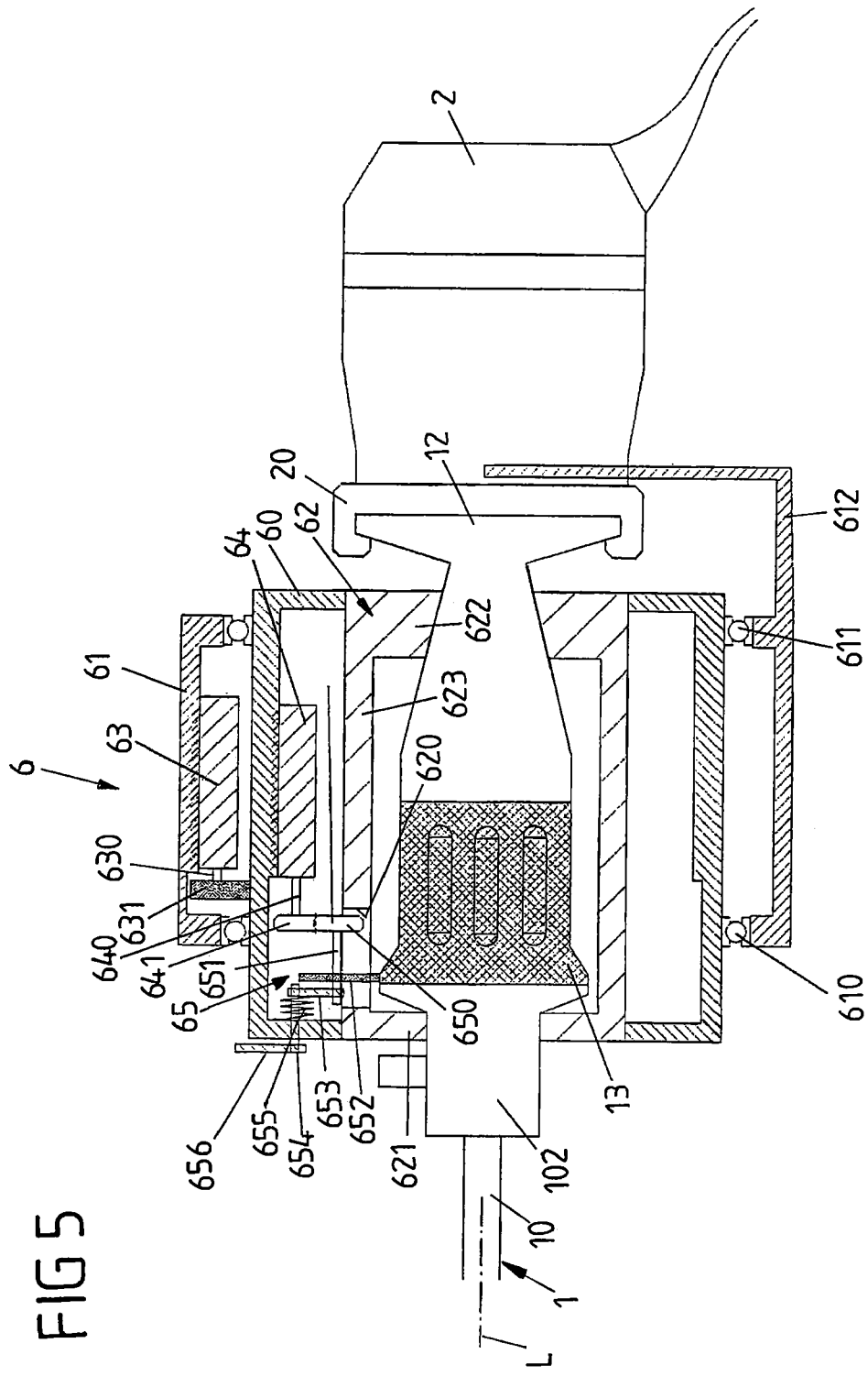
FIG. 5 shows a schematic sectional illustration of a further rotational device for rotating an endoscope.

FIG. 5 shows a schematic sectional illustration of a rotational device 6 which, in terms of some features and properties, is similar to the rotational devices depicted above on the basis of FIGS. 1 to 4. The type of illustration, in particular the sectional plane, corresponds to that in FIGS. 3 and 4. In particular, an endoscope 1 and a camera device 2 are also indicated by contours in FIG. 5, only an operating element 13 is highlighted by texture. The following illustrates in particular features and properties in which the rotational device 6 differs from the rotational devices depicted above on the basis of FIGS. 1 to 4.

The rotational device 6 depicted in FIG. 5 differs from the rotational devices depicted above on the basis of FIGS. 3 and 4 in that, in particular, it is embodied for a differently designed endoscope 1. Apart from that, the rotational device 6, in particular, substantially has the same design and function as the rotational device 6 as per FIG. 3, and so reference is made to the explanations above in this respect.

The endoscope 1 depicted in FIG. 5 has an interlocking section 102, which, in respect of a rotation about the longitudinal axis L of the endoscope 1, can be coupled to the adapter 62 in an interlocking manner such that, as a result of rotational motion of the adapter 62 about the longitudinal axis L, the shaft 10 of the endoscope 1 is picked up and, in this manner, the endoscope 1 is rotated about its longitudinal axis L. By way of example, the interlocking section has a hexagonal or other polygonal outer contour in a sectional plane orthogonal to the sectional plane in FIG. 5 and orthogonal to the longitudinal axis L.

In the rotational devices 6 depicted on the basis of FIGS. 3 to 5, a first drive means 63 is arranged at a stationary assembly 61 and a second drive means 64 is arranged at a rotatable assembly 60. In order to rotate the endoscope 1 about the longitudinal axis L, the first drive means 63 is driven, more particularly exclusively driven, while the second drive means 64 is not operated if the swivel prism 11 should not be adjusted simultaneously by means of the operating element 13. If the operating element 13 is to be actuated, the second drive means 64 is driven. If the endoscope 1 is to be rotated and, simultaneously, the operating element 13 is to be actuated, the drive means 63, 64 are operated simultaneously, but independently of one another.

Figure 6:
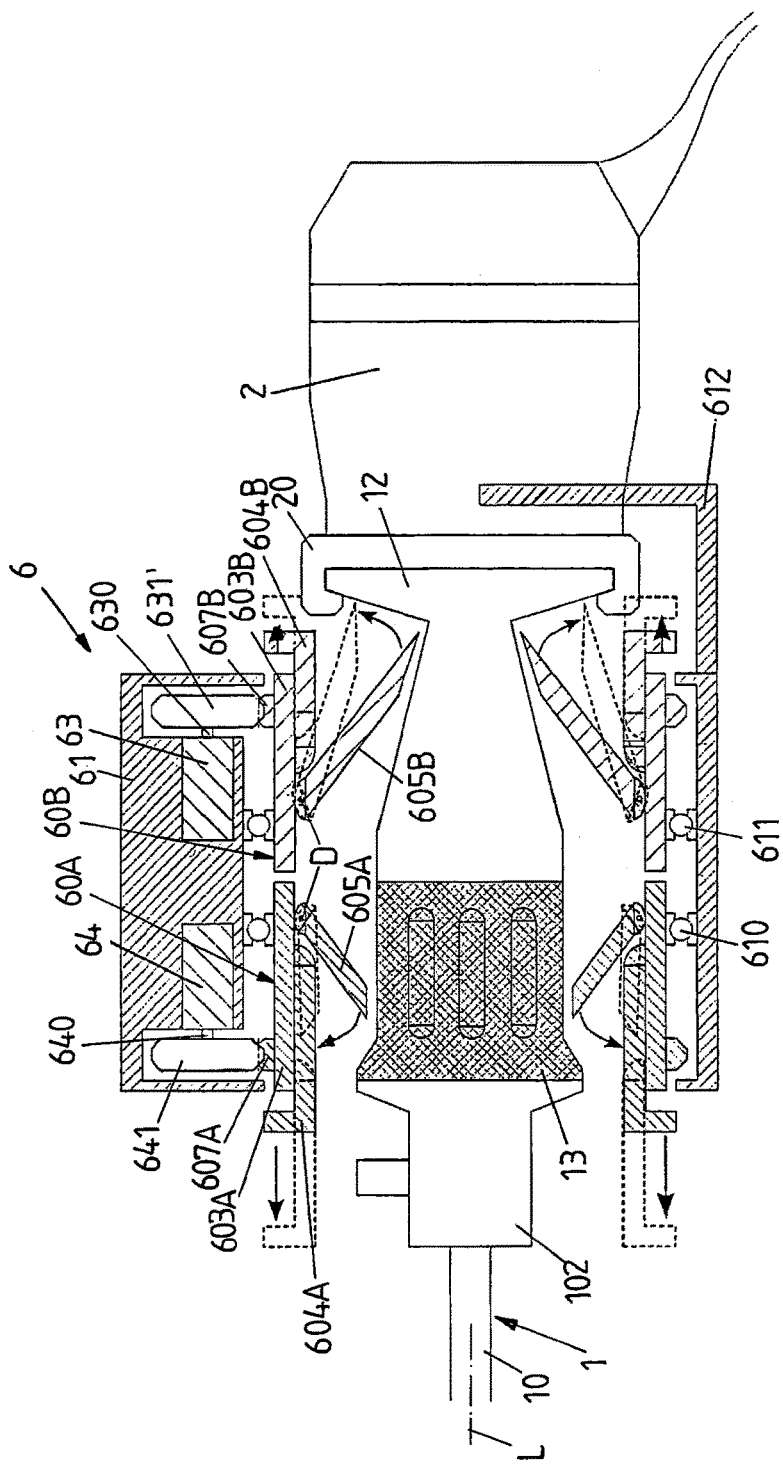
FIG. 6 shows a schematic sectional illustration of a further rotational device for rotating an endoscope.

FIG. 6 shows a schematic sectional illustration of a rotational device 6 which, in terms of some features and properties, is similar to the rotational devices depicted above on the basis of FIGS. 1 to 5. The type of illustration, in particular the sectional plane, corresponds to that in FIGS. 3 to 5. In particular, an endoscope 1 and a camera device 2 are also indicated by contours in FIG. 6; an operating element 13 of the endoscope 1 is highlighted by texture. The following illustrates in particular features and properties in which the rotational device 6 differs from the rotational devices depicted above on the basis of FIGS. 1 to 5.

In the rotational devices depicted on the basis of FIGS. 3 to 5, the first drive means 63 is arranged at the stationary assembly 61 and the second drive means 64 is arranged at the rotatable assembly 60. In contrast thereto, both the first drive means 63 and the second drive means 64 are arranged at a stationary assembly 61 in the rotational device 6 depicted in FIG. 6. The rotational device 6 comprises two rotatable assemblies 60A, 60B, of which a first rotatable assembly 60B can be put into rotational motion about the longitudinal axis L of the endoscope 1 by means of the first drive means 63 and a second rotatable assembly 60A can be put into rotational motion about the longitudinal axis L of the endoscope 1 by means of the second drive means 64.

The first rotatable assembly 60B is embodied with a ring element 603B which surrounds the endoscope 1 about the longitudinal axis L and which is mounted at the stationary assembly 61 by means of a bearing 611, in particular a roller bearing or another antifriction bearing or a sliding bearing. The first drive means 63 engages with a toothing 607B on an outer circumferential surface of the ring element 603B via a pinion 631' arranged at the driveshaft 630 of the first drive means 63. Driven by the first drive means 63, the pinion 631' rolls on the toothing 607B and rotates the ring element 603B about the longitudinal axis L.

The second drive means 64 likewise comprises a pinion 641 arranged at a driveshaft 640, which pinion engages with a toothing 607A at a ring element 603A of the second rotatable assembly 60A. Driven by the second drive means 64, the pinion 641 puts the ring element 603A into rotational motion about the longitudinal axis L.

The toothings 607A, 607B extend around the ring elements 603A, 603B such that, by means of the engagement with the assigned pinion 641, 631', the respective ring elements 603A, 603B can be rotated about the longitudinal axis L.

The first rotatable assembly 60B can be coupled to a grip piece of the shaft 10 of the endoscope 1 in an interlocking and/or force-fit manner by means of a clamping means 605B in the form of one or more clamping levers to be actuated by means of an, in particular ring-shaped, slider 604B. By means of the clamping means 605B, the first rotatable assembly 60B can therefore be secured in a rotationally secured manner on the shaft 10 such that, in the case of rotational motion of the first rotatable assembly 60B, the shaft 10 is taken along and, in this manner, the endoscope 1 is rotated about its longitudinal axis L.

The second rotatable assembly 60A can be coupled to the operating element 13 in an interlocking and/or force-fit or frictionally engaged manner by means of a clamping means 605A in the form of one or more clamping levers to be actuated by means of an, in particular ring-shaped, slider 604A in such a way that, in the case of rotational motion of the second rotatable assembly 60A, the operating element 13 is taken along and, in this manner, the swivel prism 11 (cf. FIGS. 2 to 4) to be adjusted by the operating element 13 is adjusted.

The clamping levers 605A, 605B are respectively hinged in a pivotable manner on the associated rotatable assembly 60A, 60B about an in particular tangentially arranged pivot axis D and they are pretensioned in a spring-elastic manner in a direction away from an abutting position, in which the clamping levers 605A, 605B abut against the shaft 10 and the operating element 13, respectively.

In the rotational device 6 depicted in FIG. 6, the camera device 2 is also is kept stationary in terms of position in relation to the stationary assembly 61 by means of a support section 612. Driven by the first rotational device 63, the endoscope 1 is therefore rotated relative to the camera device 2. The coupling means 20 of the camera device 2 guides the proximal end of the endoscope 1, which may be embodied as an eyepiece 12 pursuant to DIN 58105, in the axial and radial direction, but permits rotational motion relative to the camera device 2.

FIG. 7 shows a schematic sectional illustration of a rotational device 6 which, in terms of some features and properties, is similar to the rotational devices depicted above on the basis of FIGS. 1 to 6. The type of illustration, in particular the sectional plane, corresponds to that in FIGS. 3 to 6. In particular, an endoscope 1 and a camera device 2 are also indicated by contours in FIG. 7; an operating element 13 of the endoscope 1 is highlighted by texture. The following illustrates in particular features and properties in which the rotational device 6 differs from the rotational devices depicted above on the basis of FIGS. 1 to 6.

The rotational device 6 depicted in FIG. 7 differs from the rotational device depicted on the basis of FIG. 6 in that, in particular, adapters 606A, 606B are provided in place of the clamping means 605A, 605B. The adapters 606A, 606B are provided and embodied to respectively establish an operative connection, in particular for the interlocking and/or force-fit transmission of torques, between the rotatable assemblies 60A, 60B on the one hand and the shaft 10 of the endoscope 1 and the operating element 13, respectively, on the other hand. Apart from this, the rotational device 6 is, in particular, similar or identical in terms of the features and the functionality thereof to the rotational device 6 depicted above on the basis of FIG. 6 such that reference is made to the explanations above.

FIGS. 8A to 14 show schematic illustrations of a rotational device 6 which, in terms of some features and properties, is similar to the rotational devices depicted above on the basis of FIGS. 1 to 7, in particular the rotational devices depicted above on the basis of FIGS. 6 and 7. The following describes, in particular, features and properties in terms of which the rotational device 6 differs from the rotational devices depicted above on the basis of FIGS. 6 and 7.

Figure 9A:
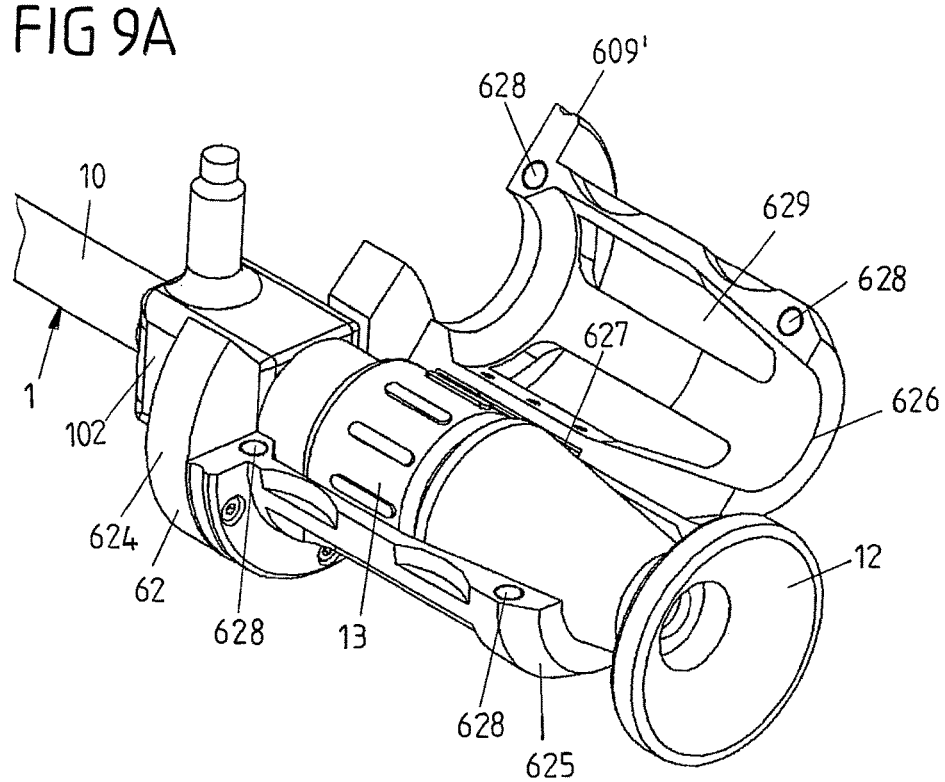
FIG. 9A shows a schematic axonometric illustration of an adapter of the rotational device from FIGS. 8A and 8B in an opened state.
Figure 9B:
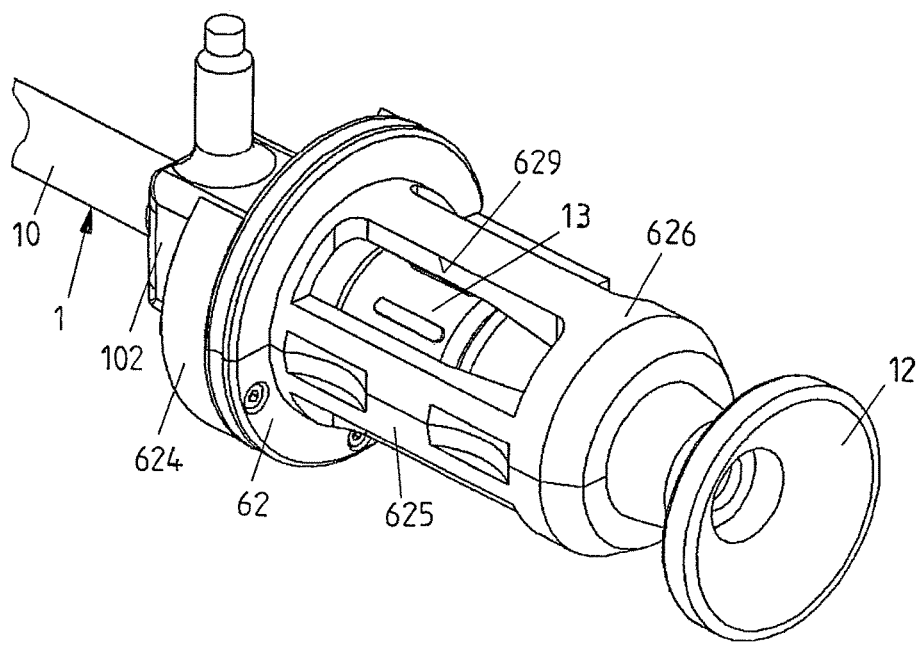
FIG. 9B shows a schematic axonometric illustration of the adapter from FIG. 9A in a closed state.
Figure 10:
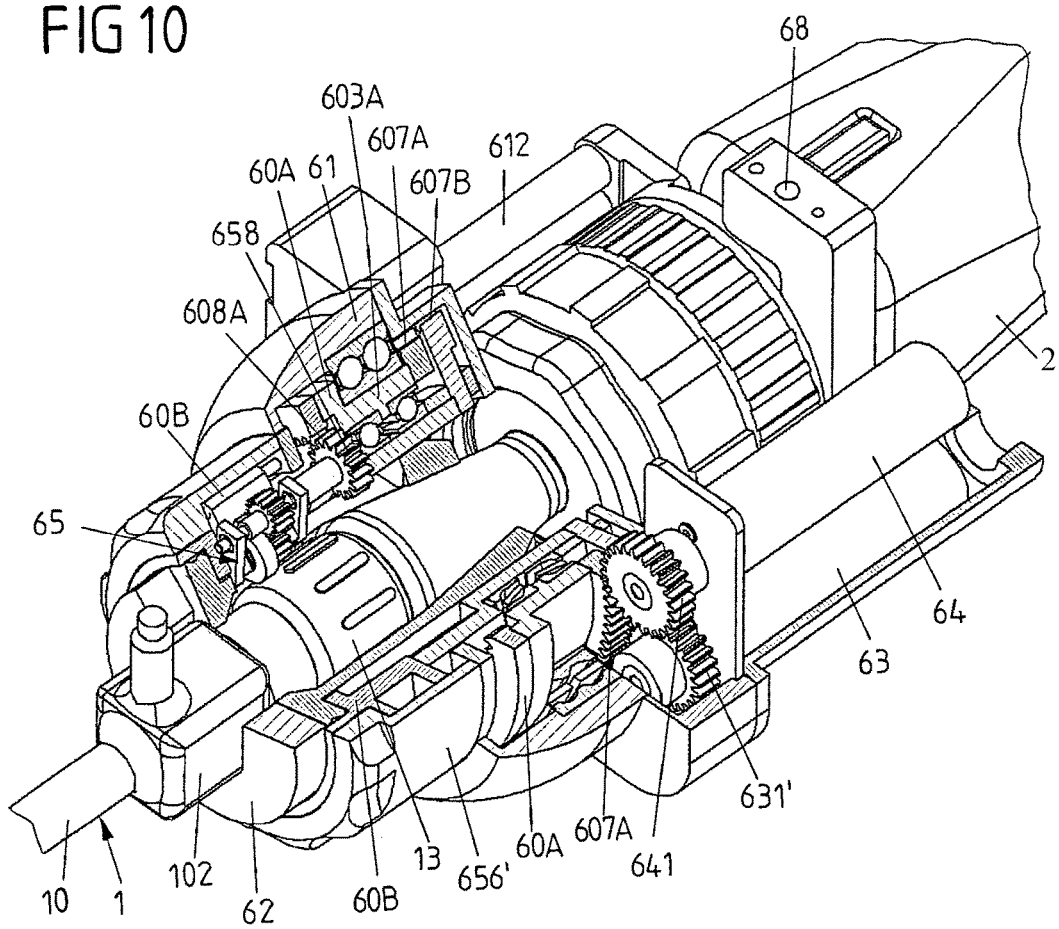
FIG. 10 shows a schematic partial sectional illustration of the rotational device from FIGS. 8A to 9B.

The rotational device 6 depicted in FIGS. 8A to 14 comprises—as can be seen, in particular, from the partial sectional view as per FIG. 10—a stationary assembly 61 which, by means of a support section 612, is kept stationary in terms of position in relation to a camera device 2. Arranged at the stationary assembly 61 is a rotatable assembly 60A, at which, in turn, a further rotatable assembly 60B is arranged in a rotatable manner.

A first drive means 63 and a second drive means 64 are arranged at the stationary assembly 61. The first drive means 63 acts on a toothing 607B of the rotatable assembly 60B by means of a pinion 631'; in particular, the pinion 631' meshes with the toothing 607B of the rotatable assembly 60B. The second drive means 64 acts on a toothing 607A of the rotatable assembly 60A by means of a pinion 641; in particular, the pinion 641 meshes with the toothing 607A of the rotatable assembly 60A. The rotatable assembly 60B driven by the first drive means 63 is connected in a force-fit or frictionally engaged and/or interlocking rotationally secured manner to an adapter 62, which in turn surrounds the shaft 10 of the endoscope 1 in a rotationally secured manner (in particular in an interlocking rotationally secured manner) and is thus connected to the endoscope 1 in a rotationally secured manner. The rotatable assembly 60A driven by the second drive means 64 acts on a pinion 658 of a friction wheel mechanism 65 by means of a toothing 608A, which, as an inner toothing, runs around the ring element 603A of the rotatable assembly 60A. The friction wheel mechanism comprises a friction wheel 652 and has a frictionally engaged connection to an operating element 13 of the endoscope 1 by means of the friction wheel 652.

Figure 11:
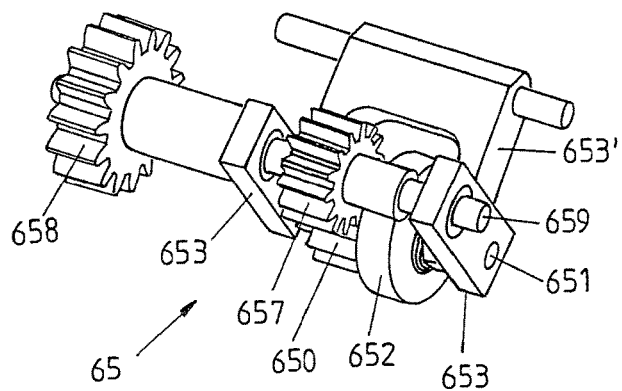
FIG. 11 shows a schematic axonometric illustration of a friction wheel mechanism of the rotational device from FIGS. 8A to 10.

FIG. 11 shows a separate view of the friction wheel mechanism 65. The pinion 658 engages with the toothing 608A, embodied as inner toothing, of the rotatable assembly 60A (cf. FIG. 10) and it is put into rotational motion in the case of rotational motion of the rotatable assembly 60A. The pinion 658 drives a shaft 659, at which a gearwheel 657 is arranged, which toothed wheel engages with a gearwheel 650 on a shaft 651. The friction wheel 652 is arranged at the shaft 651 in such a way that the friction wheel 652 can be driven and put into rotational motion by a rotational motion of the gearwheel 650. The shaft 651 is held by a lever 653 which is pivotable about the shaft 659 and therefore said shaft 651 is movable about the shaft 659 on a circular arc section. Together with a lever 653', the lever 653 forms a knee lever.

By pivoting the lever 653 about the shaft 659, the friction wheel 652 can be put into abutment or out of abutment with the operating element 13. In this case, the end of the lever 653' facing away from the shaft 651 is hinged on a handwheel 656' (cf. FIGS. 8A, 8B, 10, 13A, 13B, 14) which is rotatable relative to the rotatable assembly 60B about the longitudinal axis L. By contrast, the shaft 659 is mounted in a manner secured in terms of position on the rotatable assembly 60B. Therefore, rotating the handwheel 656' relative to the rotatable assembly 60B about the longitudinal axis L can modify the position of the knee lever 653, 653' and thereby move the friction wheel 652 closer to the operating element 13 or further away from the operating element 13.

Figure 12A:
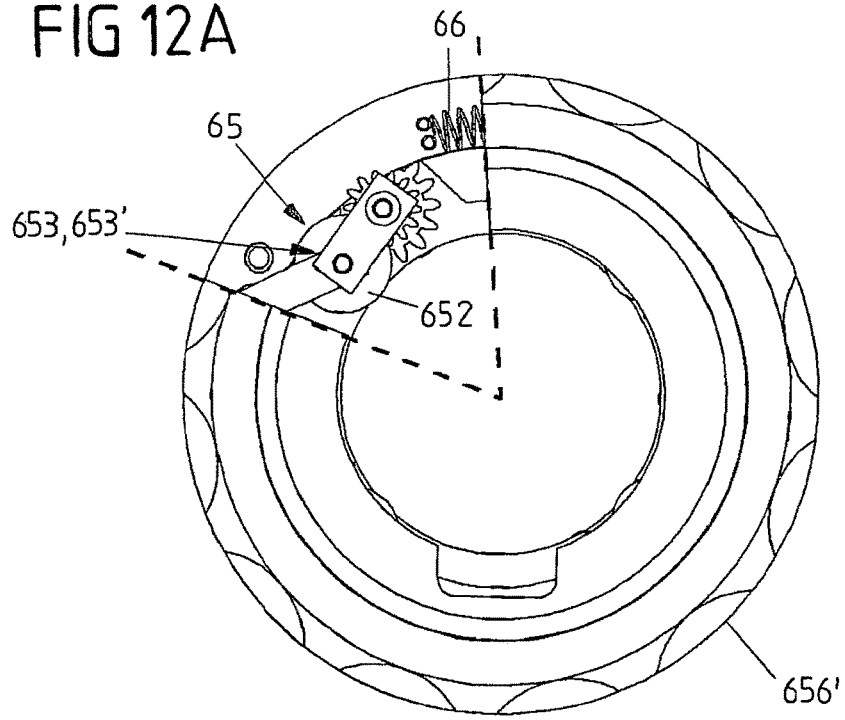
FIG. 12A shows a further schematic illustration of the friction wheel mechanism from FIG. 11 in a state in which the friction wheel mechanism does not abut against an endoscope.
Figure 12B:
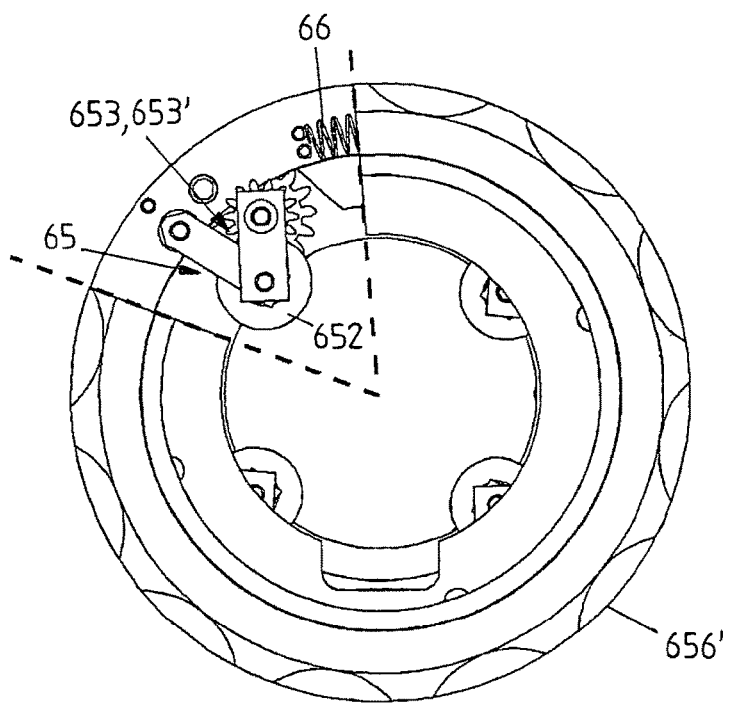
FIG. 12B shows a further schematic illustration of the friction wheel mechanism from FIGS. 11 and 12A, in a state in which the friction wheel mechanism is to be brought into abutment with an endoscope.

This is depicted in FIGS. 12A and 12B. Here, FIG. 12A shows a position of the handwheel 656', in which the friction wheel 652 is distant from the operating element 13 (cf. FIG. 10). FIG. 12B shows a position of the handwheel 656' in which the friction wheel 652 is offset radially inward and therefore brought into a position in which it, when an endoscope 1 is placed against the rotational device 6, is in frictional abutment with the operating element 13 and therefore coupled to the latter in a force-fit or frictionally engaged manner.

The rotational device 6 comprises four friction wheel mechanisms 65, which are arranged on the rotatable assembly 60B offset in the circumferential direction and which can be adjusted simultaneously by means of the handwheel 656'.

The endoscope 1 is coupled in a rotationally secured manner to the rotatable assembly 60B by means of the adapter 62. As can be seen in the illustrations of FIGS. 9A and 9B, the adapter 62 has a cage-like design with cutouts 629, through which the friction wheel mechanisms 65 can engage in order to bring the friction wheel 652 of each friction wheel mechanism 65 into frictional abutment with the operating element 13.

The adapter 62 has two adapter parts 625, 626, which are connected to one another in a hinged manner by means of a hinge 627. In the closed state—depicted in FIG. 9B—the adapter parts 625, 626 engage around a grip piece of an endoscope 1 on the circumference, wherein magnets 628 which hold the adapter parts 625, 626 against one another in the closed state are provided on the adapter parts 625, 626.

An interlocking section 624, which is to be brought into an interlocking engagement with an interlocking section 102 of the endoscope 1 in order thus to couple the endoscope 1 in an interlocking rotationally secured manner to the adapter 62, is arranged on an adapter part 625.

As can be seen from FIG. 14, the endoscope 1, together with the adapter parts 625, 626 arranged thereon, can be placed against, or inserted into, the rotational device 6 in an insertion direction E in order, in this manner, to detachably fasten the endoscope 1 at the rotational device 6.

In order to place the endoscope 1 together with the adapter 62 arranged thereon at the rotational device 6, the handwheel 656' is actuated in order to move the friction wheels 652 of the friction wheel mechanisms 65 radially outward as far as the state depicted in FIG. 12A. Once the endoscope 1, together with the adapter 62, has been inserted into the receptacle opening provided by the rotatable assembly 60B (cf. FIG. 10), the handwheel 656' is adjusted, in particular rotated, in such a way that the friction wheels 652 are moved radially inward and therefore come into abutment with the operating element 13 in accordance with the state depicted in FIG. 12B.

Here, the handwheel 656' is pretensioned in the direction of the abutting position by means of springs 66 (cf. FIGS. 12A and 12B) such that, when the handwheel 656' is released, the friction wheels 652 are automatically moved radially inward and therefore in the direction of the abutting position thereof with the operating element 13.

Figure 13A:
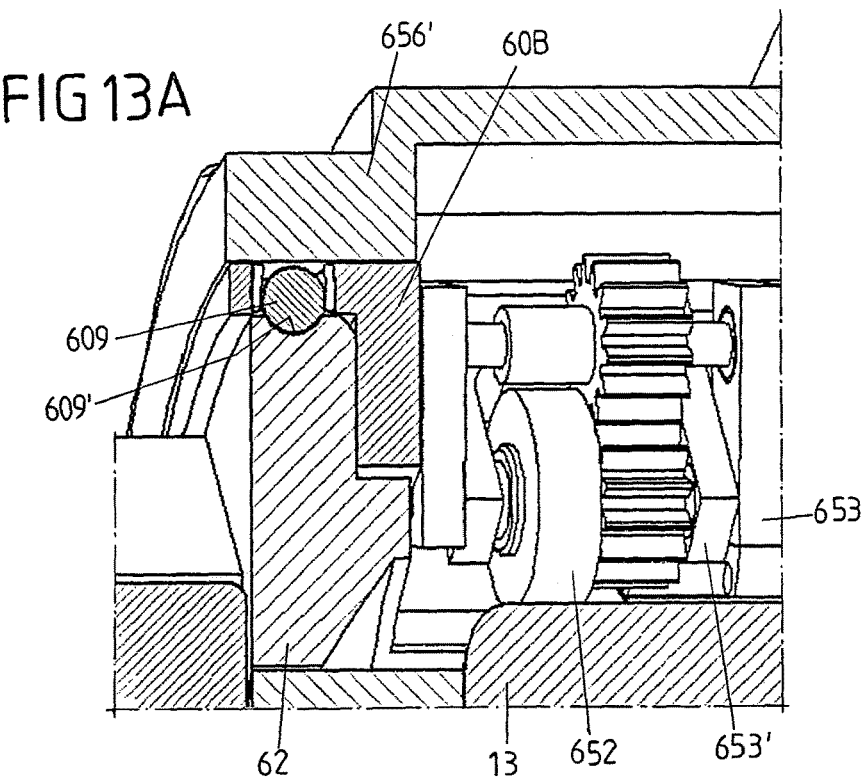
FIG. 13A shows a further schematic axonometric sectional illustration of a section of the rotational device from FIGS. 8A to 12B, depicting the coupling of the adapter to a rotatable assembly of the rotational device.
Figure 13B:
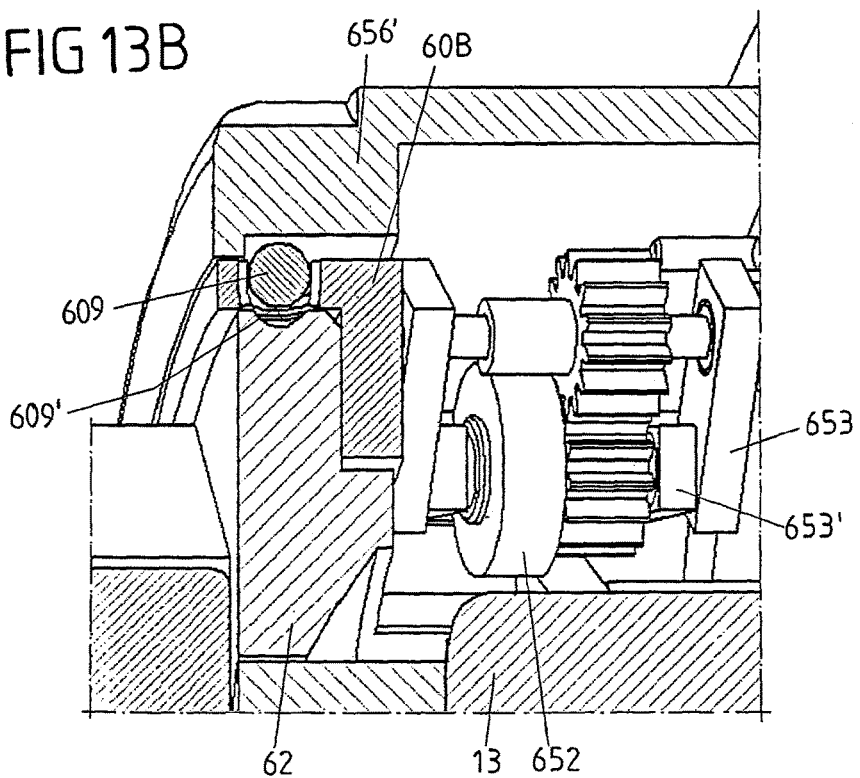
FIG. 13B shows a further schematic axonometric sectional illustration of the section depicted in FIG. 13A when the coupling has been lifted.

If the friction wheels 652 are in frictional engagement with the operating element 13, the adapter 62 is also locked in the axial direction relative to the rotatable assembly 60B by means of an axial protection 609, which can be identified in FIGS. 13A and 13B. The axial protection 609 comprises spheres which are held in the positions shown in FIG. 13A by the handwheel 656', in which positions they engage in a groove 609' at the adapter 62. When lifting the frictionally engaged connection between the friction wheels 652 and the operating element 13 by rotating the handwheel 656', the axial protection 609 is also brought out of engagement with the groove 609' by virtue of the spheres being movable out in a radially outward direction and therefore being movable out of the groove 609'. Subsequently, removing the adapter 62 from the rotatable assembly 60B is possible parallel to the longitudinal axis L.

If, in one of the rotational devices depicted on the basis of FIGS. 6, 7, 8A, 8B to 14, in which the drive means 63, 64 are respectively arranged at the stationary assembly, the endoscope 1 is intended to be rotated about the longitudinal axis L thereof but the swivel prism 11 is not intended to be adjusted in the process, it is necessary for the first drive means 63 and the second drive means 64 to be driven for an identical motion of the shaft 10 and of the operating element 13 so that no relative motion occurs between the shaft 10 and the operating element 13 of the endoscope 1. If relative motion is effected between the operating element 13 and the shaft 10, this results in adjustment of the swivel prism 11 and of the direction of view. An embodiment of the drive means 63, 64 as stepper motors facilitates a precise drive and a precise control of the rotation of the shaft 10 and of the swiveling of the swivel prism 11 by means of the operating element 13.

Figure 15:
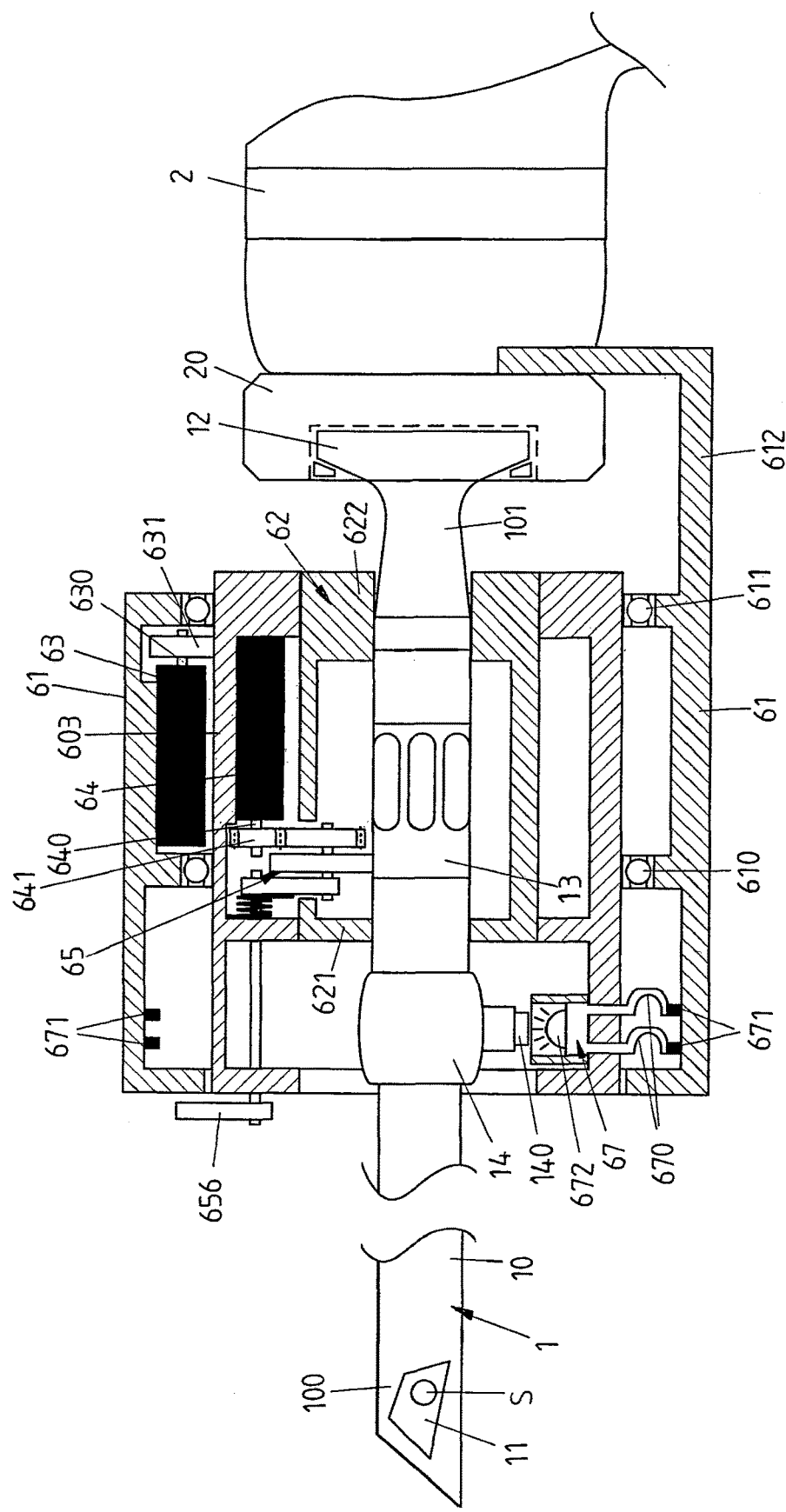
FIG. 15 shows a schematic sectional illustration of a further rotational device which additionally comprises a light source for coupling light into an endoscope.

FIG. 15 shows a schematic sectional illustration of a rotational device 6 which, in terms of some features and properties, is similar to the rotational devices depicted above on the basis of FIGS. 1 to 14. The type of illustration, in particular the sectional plane, corresponds to that in FIGS. 3 to 7. In particular, an endoscope 1 and a camera device 2 are also indicated by contours in FIG. 15. The following illustrates in particular features and properties in which the rotational device 6 differs from the rotational devices depicted above on the basis of FIGS. 1 to 14.

The rotational device 6 depicted in FIG. 15 differs from the rotational device depicted on the basis of FIG. 3 by, in particular, a light source 67, which is securely arranged on the rotatable assembly 60, which is in contact via contacts 670 with slip rings 671 at the stationary assembly 61 and which is supplied with electrical power via the slip rings 671 and the contacts 670. The slip rings 671 are ring-shaped and arranged at the stationary assembly 61 in such a way that, in the case of a rotation of the rotatable assembly 60 relative to the stationary assembly 61, the contacts 670 glide in a slipping manner along the slip rings 671 and are continuously in electrically conductive contact with the slip rings 671.

The light source 67 comprises a lamp or a luminous means 672, which faces an input 140 on an interface 14 of the endoscope 1 and which is able to couple light into this input 140. In particular, the lamp comprises one or more light-emitting diodes or semiconductor lasers or other lasers. When the endoscope 1 is rotated with the rotatable assembly 60 as a result of the rotationally secured coupling of the rotatable assembly 60 with the shaft 10 of the endoscope 1 by way of the adapter 62—the light source 67 is moved in a manner identical to the shaft 10 of the endoscope 1. Therefore, the positional relationship between the light source 67 and the input 140 is maintained in the case of a rotation of the endoscope 1 with the rotatable assembly and light from the light source 67 can be coupled into the input 140 of the endoscope 1.

The light source 67 renders possible an illumination of an operating site by means of the endoscope 1. To this end, the light from the lamp 672 shone into the input 140 is guided through the shaft 10 of the endoscope 1 to the distal end 100 of the endoscope 1 such that the light can emerge from the shaft 10 at the distal end 100 and thus reach an operating site. Integrating a light source 67 into the rotatable assembly 60 facilitates unrestricted rotating of the endoscope 1 and therefore improves the operability of the rotational device 6.

Apart thereof, the rotational device depicted in FIG. 15 has, in particular, the same design and function as the rotational device illustrated on the basis of FIG. 3 such that reference is made to the explanations above.

The idea underlying the invention is not restricted to the exemplary embodiments explained above, but can also find use in endoscope and rotational devices with other features and properties. Thus, a rotational device of the type described here is, in particular, not restricted to the use in medical endoscopes, but can also be used in technical endoscopes in the field of e.g. technical inspection and manufacturing.

The position and/or the orientation of the rotational device in space can be registered or measured by virtue of, for example, optical trackers being used, which optical trackers are fastened by means of a tracker holder 68 (see e.g. FIG. 10) on the housing of the rotational device or of the camera device. In this manner, each recorded or registered image can be assigned the corresponding position in space if the current rotational position of the endoscope and the position of the swivel prism are known. In this manner, it is possible to combine, for example superimpose or integrate, images registered by means of the endoscope with data records obtained prior to surgery (e.g. recorded using imaging methods such as CT, MRI or the like).

In order to register the rotational position of the rotatable assembly 60 and of an endoscope coupled thereto, and in order to register the position of a swivel prism, provision can respectively be made for a mechanical end stop. In particular, an end stop is provided within the rotational device and it facilitates exact determination of the rotational angle of the endoscope in relation to the camera device. By way of example, this can be realized by means of a reference rotation, the process of which may be stored in a control unit and which is initiated automatically, e.g. when switching on the supply voltage of the rotational device. Particularly if a stepper motor is used in the first drive means 63, each future driven-to position can be registered by counting the steps when proceeding from an end stop. By way of example, the end stop can be constructed in such a way that it permits a rotation through approximately 380° such that a full rotation of the endoscope is possible, and therefore the field of view is not restricted.

LIST OF REFERENCE SIGNS

1 Endoscope
10 Shaft of the endoscope 1
100 Distal end of the endoscope 1
101 Proximal end of the endoscope 1
102 Interlocking section of the endoscope 1
11 Swivel prism at the distal end 100 of the endoscope 1
12 Eyepiece at the proximal end 101 of the endoscope 1
13 Operating element at the endoscope 1
14 Interface
140 Input
2 Camera device
20 Coupling means of the camera device 2
3 Holder for holding the rotational device 6
4 Control unit for controlling the rotational device
4b Evaluation unit for evaluating an image signal from the camera device 2 and for generating an image signal for the display device 5
5 Display device for displaying an image, controlled by the evaluation unit 4b
6 Rotational device for rotating the endoscope 2
60, 60A, 60B Rotatable assembly of the rotational device 6
601, 602 Limb or radially inwardly projecting collar or support section on the rotatable assembly 60
603 Barrel surface of the rotatable assembly 60
603A, 603B Ring element of the rotatable assembly 60A, 60B
604A, 604B Slider on the ring element 603A, 603B for moving the clamping means 605A, 605B
605A, 605B Clamping means (clamping element)
606A, 606B Adapter 607A, 607B Toothing on the ring element 603A, 603B
608A Toothing
609 Axial protection
609' Groove
61 Stationary assembly of the rotational device 6
610, 611 Bearing between the stationary assembly 61 and the rotatable assembly 60
612 Support section on the stationary assembly 61 for holding a camera device 2
62 Adapter of the rotational device 6
620 Opening at the adapter 62
621, 622 Limb or radially inwardly projecting collar or support section on the adapter 62
621', 622' Clamping means (clamping limbs)
623 Barrel surface
624 Interlocking section
625, 626 Adapter part
627 Hinge
628 Magnet
629 Cutout
63 Drive means of the rotational device 6 for rotating the rotatable assembly 60
630 Driveshaft of the drive means 63
631 Friction wheel at the driveshaft 630 of the drive means 63
631' Pinion at the first drive means 63
64 Drive means of the rotational device 6 for actuating the operating element 13
640 Driveshaft of the drive means 64
641 Pinion on the driveshaft 640 of the drive means 64
65 Friction wheel mechanism of the rotational device 6 for adjusting the operating element 13
650 Gearwheel on the shaft 651
651 Shaft on the lever 353 for the gearwheel 650 and the friction wheel 652
652 Friction wheel on the shaft 651
653 Lever, pivotable about the shaft 659
653' Lever between shaft 651 and handwheel 656'
654 Shaft, about which the lever 653 is pivotable
655 Spring on the shaft 654
656 Actuation lever on the shaft 654
656' Handwheel
657 Gearwheel on the shaft 659
658 Pinion on the shaft 659
659 Shaft for the gearwheel 657 and the pinion 658
66 Spring for the handwheel 656'
67 Light source of the rotational device 6
670 Contact of the light source 67 for electric power supply of the lamp 672
671 Slip ring of the light source 67 for electric power supply of the lamp 672
672 Lamp of the light source 67
68 Tracker holder at the rotational device 6
α Viewing angle of the endoscope 1
D Pivot axis of the clamping means 605A, 605B
E Insertion direction of the endoscope 1 and of the adapter 62 into the rotational device 6
L Longitudinal axis of the endoscope 1 and rotational axis of the rotatable assemblies 60, 60A, 60B, of the ring elements 603A, 603B, of the adapter 62 and of the handwheel 656'
P Patient
R Rotational movement of the shaft 10 of the endoscope 1 about the longitudinal axis L
S Swivel axis of the swivel prism 11
V Swivel movement of the direction of view

The invention claimed is:

1. A rotational device for rotating an endoscope comprising an operating element for moving a movable assembly of the endoscope, comprising:
a rotatable assembly, to which an endoscope is connectable when inserted into the rotatable assembly;
a stationary assembly, relative to which the rotatable assembly is rotatable;
a first driver for rotating the rotatable assembly relative to the stationary assembly in order to put the endoscope connected to the rotatable assembly into rotational motion about a longitudinal axis of the endoscope;
a second driver for moving an operating element of the endoscope connected to the rotatable assembly relative to a shaft of the endoscope in order to move an assembly of the endoscope, which assembly of the endoscope is movable by the operating element;
wherein the second driver is embodied to rotate the operating element of the endoscope about the longitudinal axis of the endoscope, the operating element remaining coaxial with the longitudinal axis during rotation;
a transmission coupled to the second driver in order to exert, driven by the second driver, an adjustment force on the operating element;
wherein the transmission comprises a friction wheel arranged at a lever arm of a pivotable lever, wherein, in an abutting position of the lever, the friction wheel abuts against the operating element of the endoscope connected to the rotatable assembly, and wherein the lever is pivotable by an actuating element.

2. The rotational device according to claim 1, wherein the second driver is embodied, by way of actuating the operating element, to bring about a change in a direction of view of the endoscope by moving an optical element or a change in a focus or zoom setting of an optical system of the endoscope, the operating element provided on the endoscope for manual actuation.

3. The rotational device according to claim 1, wherein the second driver is arranged at the stationary assembly.

4. The rotational device according to claim 1, furthermore comprising:
an adapter or a clamp for rotationally secured coupling of the rotatable assembly to the endoscope.

5. The rotational device according to claim 4, wherein the adapter is removable from the rotatable assembly along the longitudinal axis in order to separate the endoscope from the rotatable assembly or joinable to the rotatable assembly along the longitudinal axis in order to mechanically couple the endoscope to the rotatable assembly.

6. The rotational device according to claim 4, wherein the adapter comprises two adapter parts movable relative to one another, which are embodied to hold the endoscope between them in a rotationally secured manner.

7. The rotational device according to claim 4, wherein the adapter, in a state connected to the rotatable assembly, is coupled to the rotatable assembly in a manner suitable for transmitting a torque about the longitudinal axis and for transmitting a force parallel to the longitudinal axis.

8. The rotational device according to claim 1, wherein the first driver is coupled via a gearing to the rotatable assembly in order to rotate the rotatable assembly about the longitudinal axis.

9. The rotational device according to claim 1, wherein the lever is elastically pretensioned toward the abutting position.

10. The rotational device according to claim 1, wherein the actuating element comprises a handwheel rotatable about the longitudinal axis, which handwheel is rotatably arranged at the rotatable assembly and movable for moving the friction wheel from the abutting position.

11. The rotational device according to claim 10, wherein the handwheel is elastically pretensioned in relation to the rotatable assembly.

12. The rotational device according to claim 1, wherein the first driver is embodied to drive a first rotatable assembly, which is mechanically connectable to the endoscope, and wherein the second driver arranged at the stationary assembly is embodied to drive a second rotatable assembly, which is coupleable to the operating element of the endoscope.

13. The rotational device according to claim 12, wherein the first and the second rotatable assembly respectively comprise a ring element rotatable about the longitudinal axis relative to the stationary assembly, which ring element is engaged via a toothing to a pinion of the respectively assigned driver and embodied to transmit a torque to the endoscope or to the operating element of the endoscope.

14. The rotational device according to claim 1, furthermore comprising a light source for generating and feeding light into the endoscope.

15. The rotational device according to claim 14, wherein the light source is arranged at the rotatable assembly and embodied to rotate with the rotatable assembly.

16. The rotational device according to claim 15, wherein the light source is electrically contacted via a contact, which abuts against a slip ring of the stationary assembly.

17. The rotational device according to claim 1, wherein the operating element is part of a user interface at an outer surface of the endoscope, and the second driver directly engages with and rotates the operating element.

18. The rotational device according to claim 1, wherein the operating element comprises an operating wheel that encircles the longitudinal axis.

19. An endoscope device comprising:
a rotational device according to claim 1;
an endoscope arranged at the rotatable assembly.

20. The endoscope device according to claim 19, wherein the endoscope comprises a shaft and an operating element for changing a direction of view of the endoscope by moving an optical element or for changing a focus or zoom setting of an optical system of the endoscope.

21. The endoscope device according to claim 20, wherein the endoscope comprises a swivel prism swivelable about a swivel axis and arranged at an end distant from the rotational device, wherein the operating element of the endoscope is movable for swiveling the swivel prism.

22. A method for handling an endoscope, comprising the following steps:
coupling an endoscope to a rotatable assembly of a rotational device;
rotating the rotatable assembly relative to a stationary assembly of the rotational device by a first driver in order to put the endoscope connected to the rotatable assembly into rotational motion about a longitudinal axis of the endoscope;
moving an operating element on an outside of the endoscope coupled to the rotatable assembly by a second driver of the rotational device in order to move an assembly of the endoscope relative to a shaft of the endoscope;
wherein the second driver rotates the operating element of the endoscope about the longitudinal axis of the endoscope, the operating element remaining coaxial with the longitudinal axis during rotation;
wherein the second driver drives a transmission coupled to the second driver in order to exert, via a friction wheel arranged at a lever arm of a pivotable lever, an adjustment force on the operating element;
wherein, in an abutting position of the lever, the friction wheel abuts against the operating element of the endoscope connected to the rotatable assembly, and wherein the lever is pivotable by an actuating element.

* * * * *